United States Patent [19]

Kitamura et al.

[11] 4,118,505
[45] Oct. 3, 1978

[54] NOVEL CYCLOPROPANECARBOXYLATES

[75] Inventors: Shigeyoshi Kitamura, Saitama; Nobushige Itaya, Nishinomiya; Yoshitoshi Okuno; Nobuo Ohno, both of Toyonaka; Takashi Matsuo, Nishinomiya; Masachika Hirano; Toshio Mizutani, both of Toyonaka; Hisami Takeda, Takarazuka, all of Japan

[73] Assignee: Sumitomo Chemical Company, Limited, Osaka, Japan

[21] Appl. No.: 636,981

[22] Filed: Dec. 2, 1975

Related U.S. Application Data

[63] Continuation-in-part of Ser. No. 461,029, Apr. 15, 1974, Pat. No. 4,003,945.

[30] Foreign Application Priority Data

Apr. 20, 1973 [JP] Japan ................................. 48-45915
May 27, 1973 [JP] Japan ................................. 48-58830
Jun. 4, 1973 [JP] Japan ................................. 48-63118

[51] Int. Cl.² .......................... C07C 69/74; A01N 9/24
[52] U.S. Cl. .............................. 424/275; 260/332.2 R; 260/340.5 R; 260/345.8 R; 260/347.4; 260/465 D; 424/282; 424/283; 424/285; 424/304; 424/306; 560/118; 560/124
[58] Field of Search ..... 260/468 H, 468 CA, 332.2 R, 260/340.5 R, 345.8 R, 347.4, 465 D; 424/275, 282, 283, 285, 304, 306; 560/118, 124

[56] References Cited

U.S. PATENT DOCUMENTS

| | | | |
|---|---|---|---|
| 3,285,950 | 11/1966 | Weber | 260/468 |
| 3,835,176 | 10/1974 | Matsuo et al. | 260/465 |
| 3,857,858 | 12/1974 | Itaya et al. | 260/332.2 |
| 3,862,174 | 1/1975 | Mizutani et al. | 260/240 |

FOREIGN PATENT DOCUMENTS

| | | | |
|---|---|---|---|
| 77,874 | 2/1974 | Denmark | 260/468 |
| 1,618,939 | 5/1972 | Fed. Rep. of Germany | 260/468 |
| 2,129,124 | 12/1971 | Fed. Rep. of Germany | 260/468 |
| 2,418,950 | 10/1974 | Fed. Rep. of Germany | 260/468 |
| 6,913,115 | 3/1970 | Netherlands | 260/468 |
| 371,813 | 9/1971 | Sweden | 260/468 |

*Primary Examiner*—Robert Gerstl
*Attorney, Agent, or Firm*—Stevens, Davis, Miller & Mosher

[57] ABSTRACT

Novel alkynyl esters of cyclopropanecarboxylic acid represented by the formula,

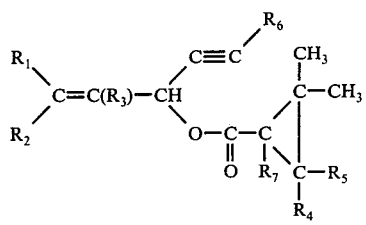

wherein $R_1$ represents hydrogen, lower alkyl having 1-4 carbon atoms, lower alkenyl having 2-4 carbon atoms, lower alkynyl having 2-4 carbon atoms, $C_1$-$C_2$ alkoxy-$C_1$-$C_4$ alkyl, $C_1$-$C_2$ alkylthio-$C_1$-$C_4$ alkyl, furyl, thienyl, furfuryl, thenyl, cyclo-$C_3$-$C_6$ alkyl, oxygen atom-containing cyclo-$C_3$-$C_6$ alkyl, cyclo-$C_5$-$C_6$ alkenyl, oxygen atom-containing cyclo-$C_4$-$C_6$ alkenyl, halo-$C_2$-$C_4$ alkenyl, phenyloxymethyl, phenylthiomethyl, cyclo-$C_5$-$C_6$ alkenylmethyl, oxygen atom-containing cyclo-$C_4$-$C_6$ alkenylmethyl, cyclo-$C_5$-$C_6$ alkylmethyl, oxygen atom-containing cyclo-$C_4$-$C_6$ alkylmethyl or

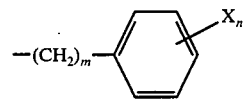

in which X is halogen, nitro, cyano, methylenedioxy, $C_1$-$C_3$ alkyl, $C_1$-$C_2$ alkoxy, dimethylamino, $m$ is 0, 1, 2 or 3, $n$ is 0, 1, 2 or 3 and each X may be different when $n$ is 2 or 3; $R_2$ and $R_3$ individually represent hydrogen, halogen (except $R_2$), phenyl, benzyl, lower alkyl having 1 - 3 carbon atoms, lower alkenyl having 2 - 3 carbon atoms, lower alkynyl having 2 - 3 carbon atoms or may form a carbon-carbon bond or are bonded to each other at the ends to form $C_3$-$C_4$ polymethylene chain, or $R_1$ and $R_2$ are bonded to each other at the ends to form $C_5$ polymethylene chain; $R_4$ represents hydrogen or methyl; $R_5$ represents hydrogen, methyl, vinyl, 1-propenyl, 2-methyl-1-propenyl, 2-methoxy-methyl-1-propenyl, 2-methoxycarbonyl-1-propenyl, 1,3-butadienyl, 2-methyl-1,3-butadienyl, 2,2-dichlorovinyl or cyclopentylidenemethyl when $R_4$ is hydrogen, and $R_5$ represents methyl when $R_4$ is methyl; and $R_6$ and $R_7$ represent hydrogen or methyl. These novel esters are produced by reacting an alcohol or its halide or arylsulfonate of the formula,

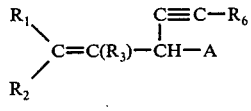

wherein $R_1$, $R_2$, $R_3$ and $R_6$ are as defined above, and A is hydroxy, halogen or arylsulfoxy, with a cyclopropanecarboxylic acid of the formula,

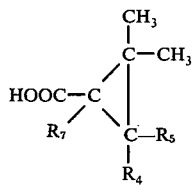

wherein $R_4$, $R_5$ and $R_7$ are as defined above, or its reactive derivative. These esters are useful as an insecticide harmless to mammals.

13 Claims, No Drawings

NOVEL CYCLOPROPANECARBOXYLATES

This application is a continuation-in-part of application Ser. No. 461,029 filed Apr. 15, 1974.

This invention relates to novel cyclopropanecarboxylic acid esters, a process for preparing the said esters, and an insecticidal composition containing the said esters.

More particularly, the invention pertains to novel alkynyl esters of cyclopropanecarboxylic acid represented by the formula (I),

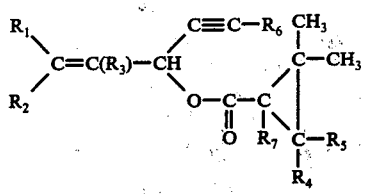

wherein $R_1$ represents hydrogen, lower alkyl having 1 - 4 carbon atoms, lower alkenyl having 2 - 4 carbon atoms, lower alkynyl having 2 - 4 carbon atoms, $C_1$-$C_2$ alkoxy-$C_1$-$C_4$ alkyl, $C_1$-$C_2$ alkylthio-$C_1$-$C_4$ alkyl, furyl, thienyl, furfuryl, thenyl, cyclo-$C_3$-$C_6$ alkyl, oxygen atom-containing cyclo-$C_3$-$C_6$ alkyl, cyclo-$C_5$-$C_6$ alkenyl, oxygen atom-containing cyclo-$C_4$-$C_6$ alkenyl, halo-$C_2$-$C_4$ alkenyl, phenyloxymethyl, phenylthiomethyl, cyclo-$C_5$-$C_6$ alkenylmethyl, oxygen atom-containing cyclo-$C_4$-$C_6$ alkenylmethyl, cyclo-$C_5$-$C_6$ alkylmethyl, oxygen atom-containing cyclo-$C_4$-$C_6$ alkylmethyl or

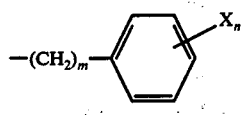

in which X is halogen, nitro, cyano, methylenedioxy, $C_1$-$C_3$ alkyl, $C_1$-$C_2$ alkoxy, dimethylamino, m is 0, 1, 2 or 3, n is 0, 1, 2 or 3 and each X may be different when n is 2 or 3; $R_2$ and $R_3$ individually represent hydrogen, halogen (except $R_2$), phenyl, benzyl, lower alkyl having 1 - 3 carbon atoms, lower alkenyl having 2 - 3 carbon atoms, lower alkynyl having 2 - 3 carbon atoms or may form a carbon-carbon bond or are bonded to each other at the ends to form $C_3$-$C_4$ polymethylene chain or $R_1$ and $R_2$ are bonded to each other at the ends to form $C_5$ polymethylene chain; $R_4$ represents hydrogen or methyl; $R_5$ represents hydrogen, methyl, vinyl, 1-propenyl, 2-methyl-1-propenyl, 2-methoxymethyl-1-propenyl, 2-methoxycarbonyl-1-propenyl, 1,3-butadienyl, 2-methyl-1,3-butadienyl,2,2-dichlorovinyl or cyclopentylidenemethyl when $R_4$ is hydrogen, and $R_5$ represents methyl when $R_4$ is methyl; and $R_6$ and $R_7$ represent hydrogen or methyl.

Various insecticides of the cyclopropanecarboxylic acid ester type have heretofore been known, and several of such esters are present also in pyrethrum components. Among many insecticides available at present, these pyrethrum components have widely been used for the control of sanitary injurious insects and agricultural and horticultural injurious insects because of their such excellent insecticidal properties that they are not only high in insecticidal activity but also low in toxicity to mammals, quick in knock-down effect on injurious insects and scarcely make the insects resistant thereto. On the other hand, however, they are expensive and hence have such drawback as being restricted in application scope. Heretofore, many attempts have been made by a large number of researchers to synthesize various homologous compounds. These attempts are directed both to the synthesis of alcohol components of the esters and to the synthesis of acid components.

From such a viewpoint that the above-mentioned drawbacks would be overcome by synthesizing esters having more excellent insecticidal effects, the present inventors made extensive studies particularly on alcohol components of the esters. As a result, the inventors have found alcohol components which are far more excellent in practicality than those in the conventional cyclopropanecarboxylic acid esters.

It is therefore an object of the present invention to provide insecticides comprising esters containing said alcohol components.

With an aim to investigate the relation between chemical structures and biological activities of cyclopropanecarboxylic acid ester type insecticides the present invention attempted the modification of side chains of α-alkynyl alcohols and examined the insecticidal effects of esters of said alcohol with various acids. As a result, the inventors have found that cyclopropanecarboxylic acid esters represented by the aforesaid formula (I) are not only far more prominent in killing effect but also more quick in knock-down effect on insects, and have confirmed that the said esters are low in toxicity to mammals and can be synthesized at low costs, and hence can be practically used not only as chemicals for controlling sanitary injurious insects but also as chemicals for controlling insects injurious to agriculture, horticulture and stored cereals. Based on the above finding, the inventors have accomplished the present invention.

The cyclopropanecarboxylates of the formula (I) are novel compounds and have stereoisomers due to the stereo structure and optical isomers due to the asymmetric carbon atom, and all of these isomers are within the scope of the invention.

Specific examples of the cyclopropanecarboxylates by the formula (I) are shown in Table 1, but the present invention is not limited thereto:

| No. | Name | Formula |
|---|---|---|
| 1 | 1-Ethynyl-2-butenyl chrysanthemate | 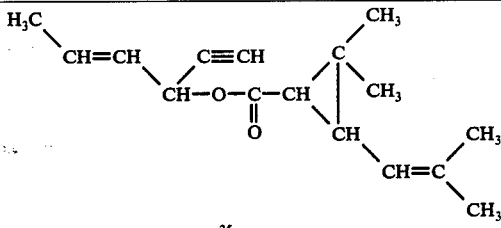 $n_D^{25}$ : 1.4816 |

-continued
| No. | Name | Formula |
|---|---|---|
| 2 | 1-Ethynyl-2-methyl-2-butenyl chrysanthemate | 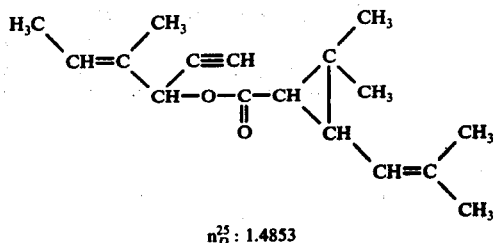 $n_D^{25}: 1.4853$ |
| 3 | 1-Ethynyl-3-methyl-2-butenyl chrysanthemate | 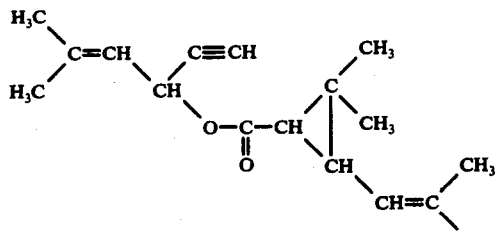 $n_D^{25}: 1.4873$ |
| 4 | 1-Ethynyl-2-methyl-2-pentenyl chrysanthemate | 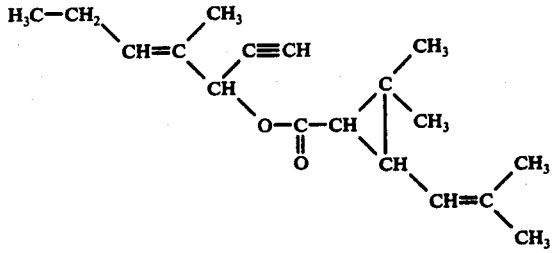 $n_D^{25}: 1.4836$ |
| 5 | 1-Ethynyl-2-ethyl-2-hexenyl chrysanthemate | 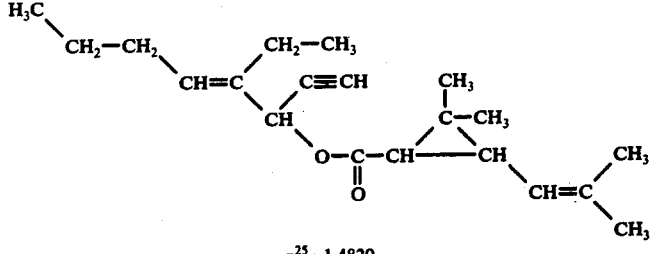 $n_D^{25}: 1.4820$ |
| 6 | 1-Ethynyl-2,4-hexadienyl chrysanthemate | 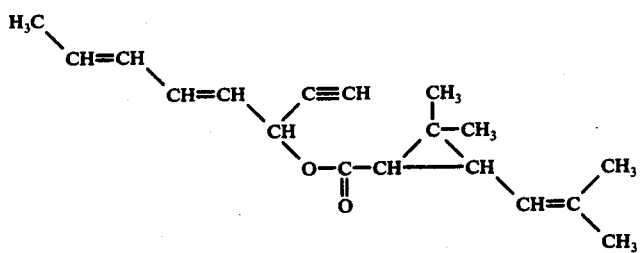 $n_D^{25}: 1.5120$ |
| 7 | 1-Ethynyl-2-isopropyl-2-propenyl chrysanthemate | 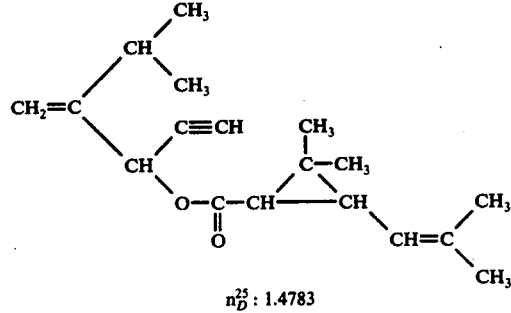 $n_D^{25}: 1.4783$ |

-continued

| No. | Name | Formula |
|---|---|---|
| 8 | 1-Ethynyl-1-(1-cyclohexenyl)-methyl chrysanthemate | $n_D^{25}$: 1.5033 |
| 9 | 1-Ethynyl-1-(1-cyclopentenyl)-methyl 2',2'-dimethyl-3'-(2''-methoxycarbonyl-1''-propenyl)-cyclopropanecarboxylate | $n_D^{25}$: 1.5015 |
| 10 | 1-Ethynyl-2-cyclohexylidene-ethyl 2',2'-dimethyl-3'-(2''-methoxymethyl-1''-propenyl)-cyclopropanecarboxylate | $n_D^{25}$: 1.5081 |
| 11 | 1-Ethynyl-2-methyl-2-butenyl 2',2',3',3'-tetramethylcyclopropanecarboxylate | $n_D^{25}$: 1.4765 |
| 12 | 1-Ethynyl-2-methyl-2-pentenyl 2',2',3'-trimethylcyclopropanecarboxylate | $n_D^{25}$: 1.4783 |
| 13 | 1-Ethynyl-2-methyl-2-butenyl 2',2'-dimethyl-3'-(1''-propenyl)-cyclopropanecarboxylate | $n_D^{25}$: 1.4802 |
| 14 | 1-Ethynyl-2-methyl-2-butenyl 2',2'-dimethyl-3'-(1'',3''-butadienyl)cyclopropanecarboxylate | $n_D^{25}$: 1.4844 |

-continued

| No. | Name | Formula |
|---|---|---|
| 15 | 1-Ethynyl-1-(1-cyclopentenyl)-methyl 2',2'-dimethyl-3'-(2''-methyl-1'',3''-butadienyl)-cyclopropanecarboxylate | 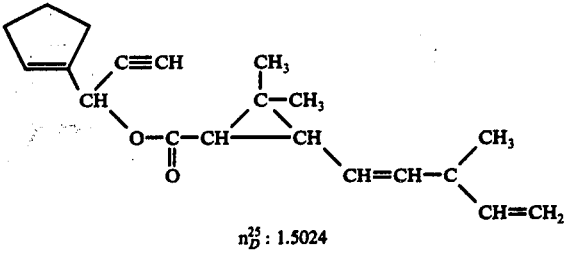 $n_D^{25}$: 1.5024 |
| 16 | 1-Ethynyl-2-methyl-2-butenyl 2',2'-dimethyl-3'-cyclopentyl-idenemethyl-cyclopropane-carboxylate | 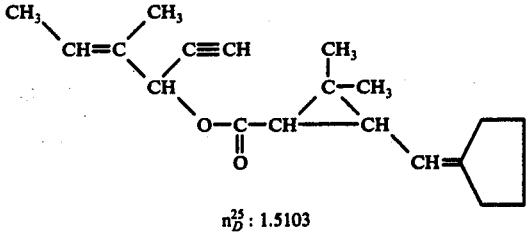 $n_D^{25}$: 1.5103 |
| 17 | 1-Ethynyl-2-methyl-2-butenyl 1',2',2',3',3'-pentamethyl-cyclopropanecarboxylate | 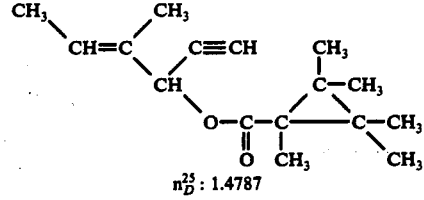 $n_D^{25}$: 1.4787 |
| 18 | 1-Ethynyl-2-methyl-2-butenyl 1',2',2'-trimethyl-3'-(2'''-methyl-1'''-propenyl)-cyclo-propanecarboxylate | 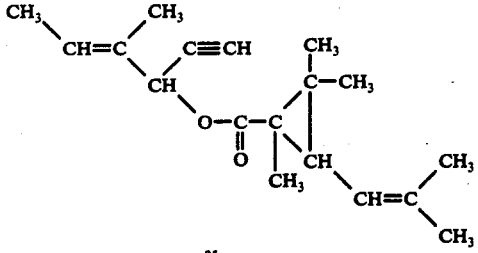 $n_D^{25}$: 1.4866 |
| 19 | 1-(1-Propynyl)-2-methyl-2-butenyl chrysanthemate | 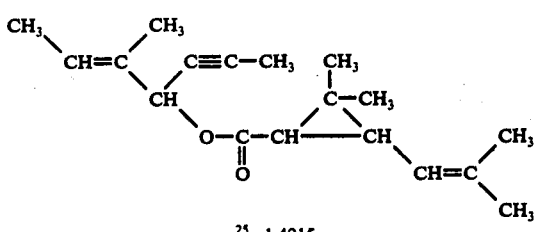 $n_D^{25}$: 1.4915 |
| 20 | 1-Ethynyl-2-methyl-2-butenyl 2',2'-dimethyl-3'-(2'',2''-dichlorovinyl)cyclopropane-carboxylate | 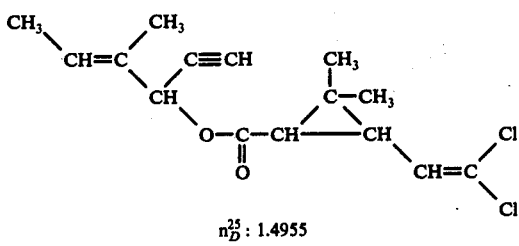 $n_D^{25}$: 1.4955 |
| 21 | 1-Ethynyl-2-methyl-2-pentenyl 2',2',3',3'-tetramethyl-cyclopropanecarboxylate | 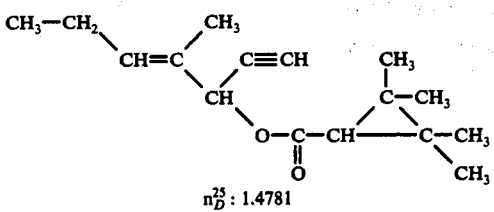 $n_D^{25}$: 1.4781 |

| No. | Name | Formula |
|---|---|---|
| 22 | 1-Ethynyl-2-methyl-2-pentenyl 2',2'-dimethyl-3'-(1''-propenyl)-cyclopropanecarboxylate | 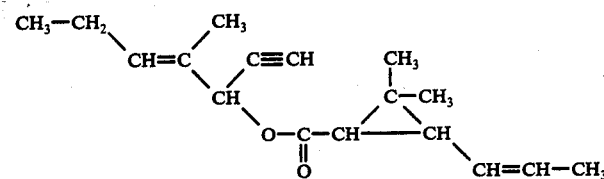 $n_D^{25}$: 1.4793 |
| 23 | 1-Ethynyl-2-methyl-2-pentenyl 2',2'-dimethyl-3'-vinyl-cyclopropanecarboxylate | 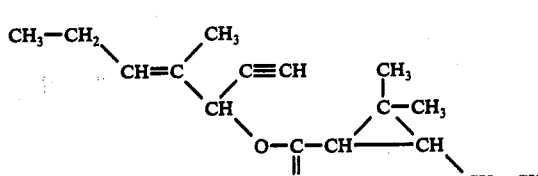 $n_D^{25}$: 1.4788 |
| 24 | 1-Ethynyl-2-methyl-2-pentenyl 2',2'-dimethyl-3'-(1'',3''-butadienyl)cyclopropane-carboxylate | 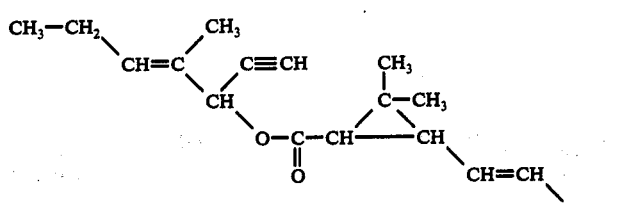 $n_D^{25}$: 1.4802 |
| 25 | 1-Ethynyl-2-methyl-2-pentenyl 2',2'-dimethyl-3'-(2''-methoxymethyl-1'''-propenyl)-cyclopropanecarboxylate | 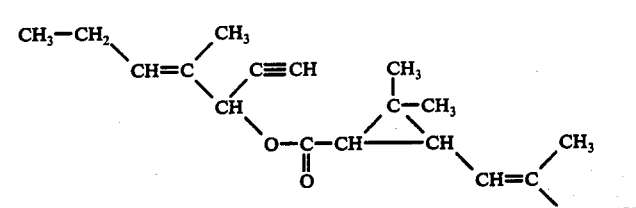 $n_D^{25}$: 1.4832 |
| 26 | 1-Ethynyl-2-methyl-2-pentenyl 2',2'-dimethyl-3'-(2''-methoxy-carbonyl-1'''-propenyl)cyclo-propanecarboxylate | 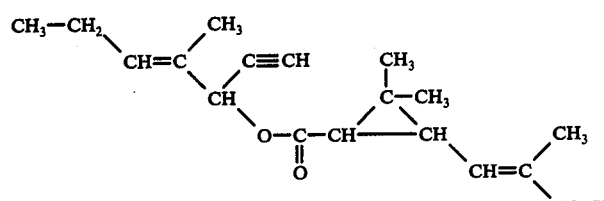 $n_D^{25}$: 1.4856 |
| 27 | 1-Ethynyl-2-methyl-2-pentenyl 2',2'-dimethyl-cyclopropanecarboxylate | 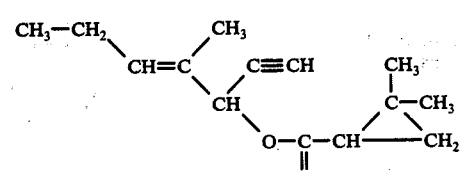 $n_D^{25}$: 1.4755 |

-continued

| No. | Name | Formula |
|---|---|---|
| 28 | 1-Ethynyl-2-methyl-2-pentenyl 2′,2′-dimethyl-3′-cyclopentylidene-methyl-cyclopropanecarboxylate | $n_D^{25}$: 1.5007 |
| 29 | 1-Ethynyl-2-methyl-2,5-hexadienyl chrysanthemate | $n_D^{25}$: 1.5036 |
| 30 | 1-Ethynyl-3-propargylallyl chrysanthemate | $n_D^{25}$: 1.5124 |
| 31 | α-Ethynylcinnamyl chrysanthemate | $n_D^{25}$: 1.5323 |
| 32 | α-Ethynyl-β-methylcinnamyl chrysanthemate | $n_D^{25}$: 1.5365 |

-continued
| No. | Name | Formula |
|---|---|---|
| 33 | α-Ethynyl-β-methyl-4-methylcinnamyl chrysanthemate | 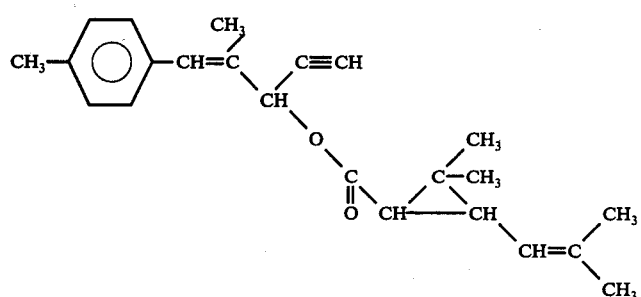<br>$n_D^{25}$: 1.5343 |
| 34 | α-Ethynyl-β-methyl-2-chlorocinnamyl chrysanthemate | 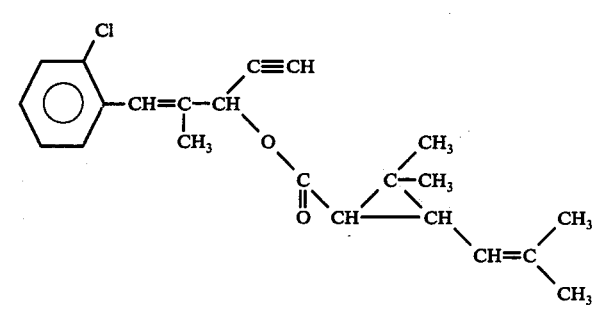<br>$n_D^{25}$: 1.5410 |
| 35 | α-Ethynyl-β-methyl-3,4-methylenedioxycinnamyl chrysanthemate | 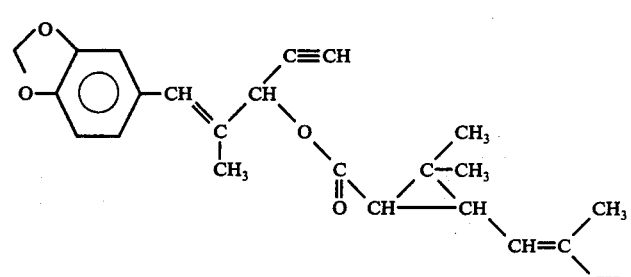<br>$n_D^{25}$: 1.5441 |
| 36 | α-Ethynyl-β-bromocinnamyl chrysanthemate | 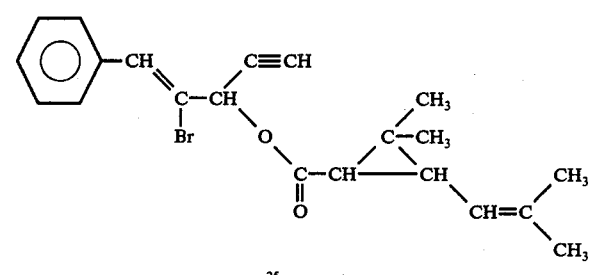<br>$n_D^{25}$: 1.5606 |
| 37 | α-Ethynyl-β-methyl-3,4-dimethoxycinnamyl chrysanthemate | 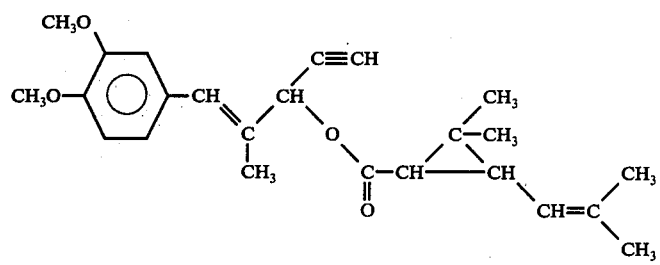<br>$n_D^{25}$: 1.5390 |

-continued

| No. | Name | Formula |
|---|---|---|
| 38 | α-Ethynyl-β-methyl-2,6-dimethyl-4-methoxycinnamyl chrysanthemate | $n_D^{25}$: 1.5404 |
| 39 | α-Ethynyl-β-methylcinnamyl 2,2,3,3-tetramethyl-cyclopropanecarboxylate | $n_D^{25}$: 1.5231 |
| 40 | α-Ethynyl-β-methylcinnamyl 2,2-dimethyl-3-cyclopentylidene-methyl-cyclopropanecarboxylate | $n_D^{25}$: 1.5350 |
| 41 | α-Ethynyl-β-methylcinnamyl 2,2-dimethyl-3-(2'-methoxy-carbonyl-1'propenyl)cyclo-propanecarboxylate | $n_D^{25}$: 1.5375 |
| 42 | α-Ethynyl-β-ethyl-4-ethoxy-cinnamyl 2,2,3-trimethyl-cyclopropanecarboxylate | $n_D^{25}$: 1.5405 |
| 43 | α-Ethynyl-β-methyl-3-nitro-cinnamyl 2',2'-dimethyl-3'-(1''-propenyl)cyclopropane-carboxylate | $n_D^{25}$: 1.5438 |

-continued

| No. | Name | Formula |
|---|---|---|
| 44 | α-Ethynyl-β-methyl-4-dimethyl-aminocinnamyl 2',2'-dimethyl-3'-(1'',3''-butadienyl)cyclopropane-carboxylate | $n_D^{25}: 1.5452$ |
| 45 | α-Ethynyl-β-methyl-4-cyano-cinnamyl 2',2'-dimethyl-3'-(2''-methyl-1'',3''-butadienyl)-cyclopropanecarboxylate | $n_D^{25}: 1.5410$ |
| 46 | α-Ethynyl-β-methyl-4-iso-propylcinnamyl chrysanthemate | $n_D^{25}: 1.5290$ |
| 47 | α-Ethynyl-β-vinylcinnamyl 2,2-dimethyl-3-(2'-methoxy-methyl-1'-propenyl)cyclo-propanecarboxylate | $n_D^{25}: 1.5371$ |
| 48 | α-Ethynyl-β-isopropylcinnamyl 2,2,3,3-tetramethylcyclopropane-carboxylate | $n_D^{25}: 1.5211$ |
| 49 | α-Ethynyl-β-propargylcinnamyl 2,2-dimethyl-3-(2'-methoxy-methyl-1'-propenyl)cyclo-propanecarboxylate | $n_D^{25}: 1.5385$ |

| No. | Name | Formula |
|---|---|---|
| 50 | α-Ethynyl-β-phenylcinnamyl 2,2,3-trimethylcyclo-propanecarboxylate | 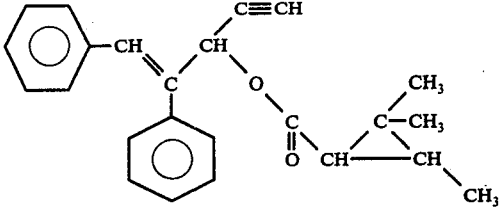<br>$n_D^{25}$: 1.5392 |
| 51 | α-Ethynyl-β-benzylcinnamyl 2,2,3,3-tetramethylcyclo-propanecarboxylate | 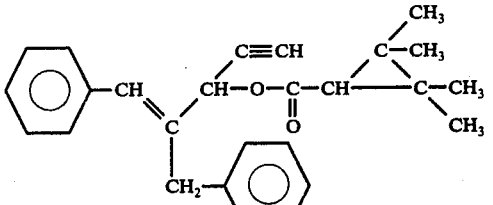<br>$n_D^{25}$: 1.5405 |
| 52 | α-Ethynyl-γ-phenylcinnamyl 2,2-dimethyl-3-(1'-propenyl)-cyclopropanecarboxylate | 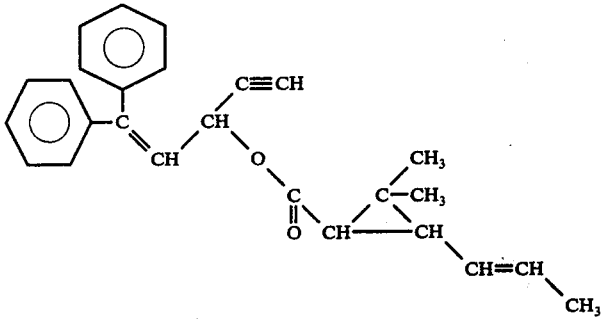<br>$n_D^{25}$: 1.5422 |
| 53 | α-Ethynyl-γ-methylcinnamyl chrysanthemate | 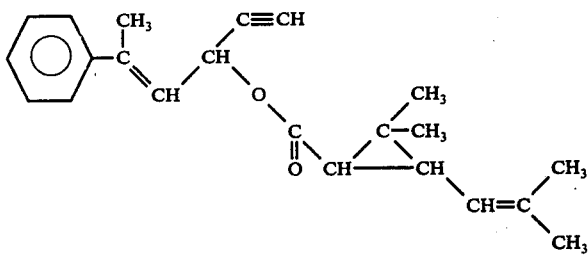<br>$n_D^{25}$: 1.5336 |
| 54 | α-Ethynyl-β-methylcinnamyl 1,2,2-trimethyl-3-(2'-methyl-1'-propenyl)cyclo-propanecarboxylate | 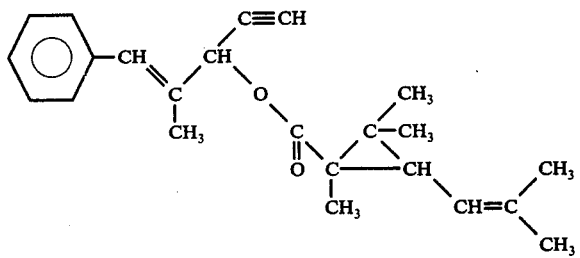<br>$n_D^{25}$: 1.5344 |

-continued

| No. | Name | Formula |
|---|---|---|
| 55 | α-Ethynyl-β-methyl-2-methyl-cinnamyl 1',2',2'-trimethyl-3'-cyclopentylidenemethyl-cyclopropanecarboxylate | 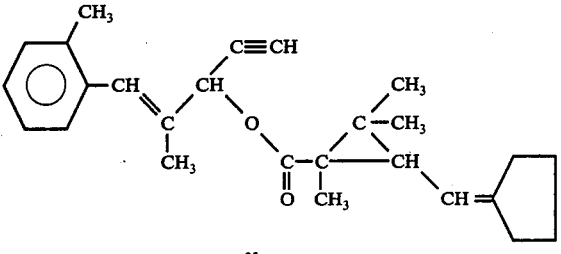<br>$n_D^{25}$: 1.5366 |
| 56 | α-Ethynyl-β-chlorocinnamyl 1,2,2,3,3-pentamethyl-cyclopropanecarboxylate | 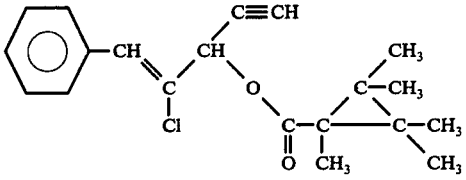<br>$n_D^{25}$: 1.5340 |
| 57 | α-Ethynyl-β-methyl-3,4-methylenedioxycinnamyl 1',2',2'-trimethyl-3'-(2''-methoxycarbonyl-1''-propenyl)-cyclopropanecarboxylate | 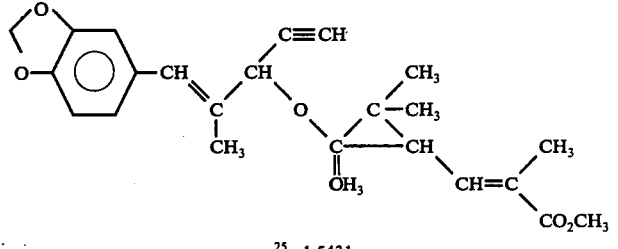<br>$n_D^{25}$: 1.5431 |
| 58 | α-(1-Propynyl)-β-methyl-cinnamyl chrysanthemate | 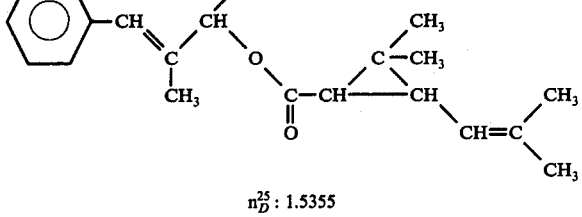<br>$n_D^{25}$: 1.5355 |
| 59 | α-Ethynyl-β-methylcinnamyl 2,2-dimethyl-3-(2',2'-dichlorovinyl)cyclopropanecarboxylate | 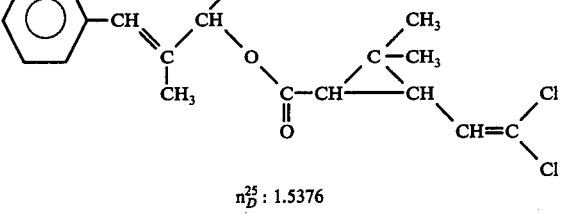<br>$n_D^{25}$: 1.5376 |
| 60 | α-Ethynyl-γ-(2-furyl)-allyl chrysanthemate | 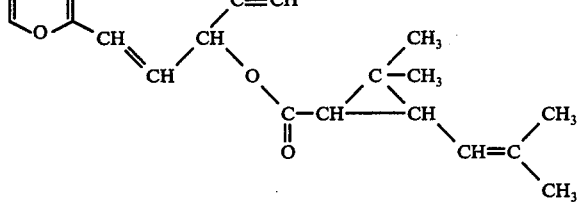<br>$n_D^{25}$: 1.5355 |

-continued
| No. | Name | Formula |
|---|---|---|
| 61 | α-Ethynyl-γ-(2-thienyl)-allyl chrysanthemate | 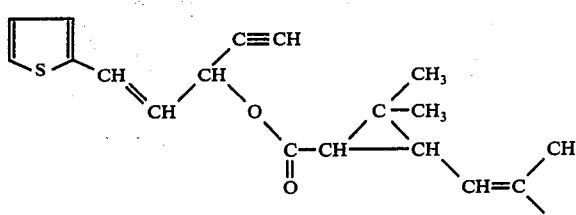<br>$n_D^{25}$: 1.5331 |
| 62 | 1-Ethynyl-4-phenyl-2-butenyl chrysanthemate | 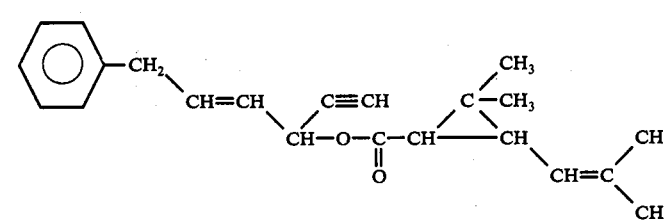<br>$n_D^{25}$: 1.5393 |
| 63 | α-Ethynyl-β-ethylcinnamyl chrysanthemate | 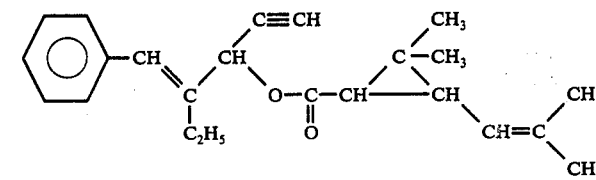<br>$n_D^{25}$: 1.5303 |
| 64 | 1-Ethynyl-2-butyn-1-yl chrysanthemate | 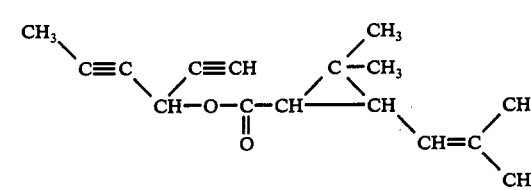<br>$n_D^{25}$: 1.4822 |
| 65 | 1-Ethynyl-2-pentyn-1-yl chrysanthemate | 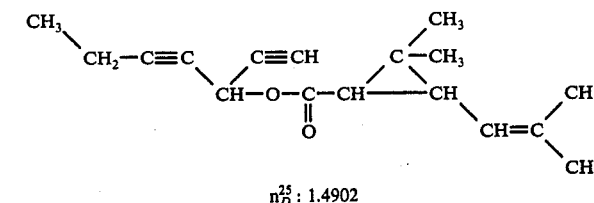<br>$n_D^{25}$: 1.4902 |
| 66 | 1-Ethynyl-2-hexyn-1-yl chrysanthemate | 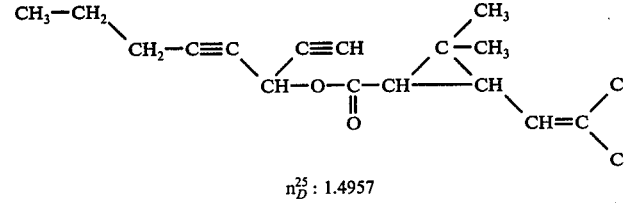<br>$n_D^{25}$: 1.4957 |
| 67 | 1-Ethynyl-2-heptyn-1-yl chrysanthemate | 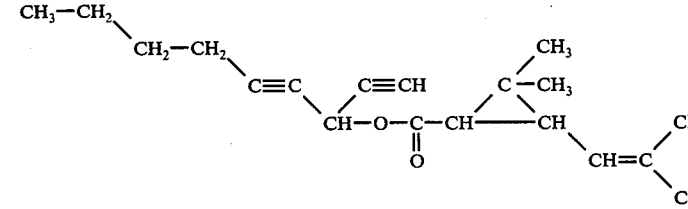<br>$n_D^{25}$: 1.5255 |

-continued

| No. | Name | Formula |
|---|---|---|
| 68 | 1-Ethynyl-4-methoxy-2-butyn-1-yl chrysanthemate | 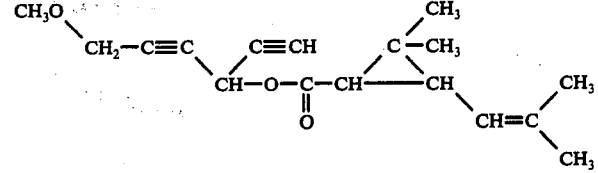<br>$n_D^{25}$: 1.5293 |
| 69 | 1-Ethynyl-5-methoxy-2-pentyn-1-yl chrysanthemate | 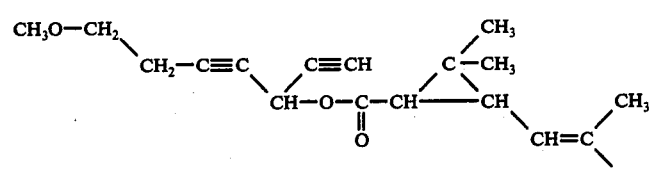<br>$n_D^{25}$: 1.5421 |
| 70 | 1-Ethynyl-4-ethoxy-2-butyn-1-yl chrysanthemate | 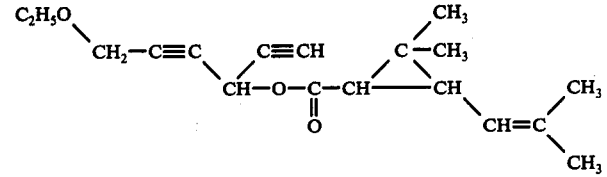<br>$n_D^{25}$: 1.5572 |
| 71 | 1-Ethynyl-5-hexen-2-yn-1-yl chrysanthemate | 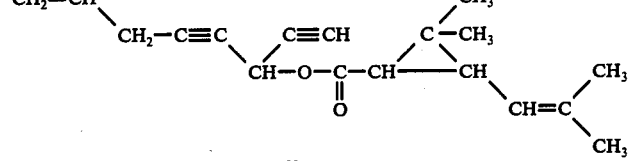<br>$n_D^{25}$: 1.4965 |
| 72 | 1-Ethynyl-2,5-hexadiyn-1-yl chrysanthemate | 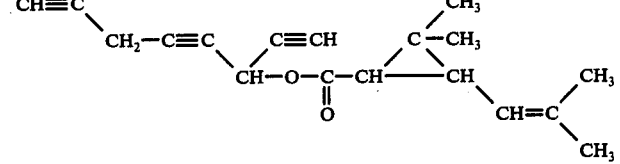<br>$n_D^{25}$: 1.5051 |
| 73 | 1-Ethynyl-6-hepten-2-yn-1-yl chrysanthemate | 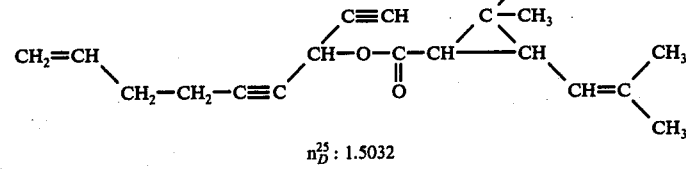<br>$n_D^{25}$: 1.5032 |
| 74 | 1-Ethynylhepta-2,6-diyn-1-yl chrysanthemate | 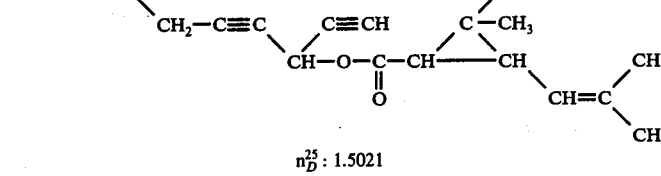<br>$n_D^{25}$: 1.5021 |
| 75 | 1-Ethynyl-6-chloro-5-hexen-2-yn-1-yl chrysanthemate | 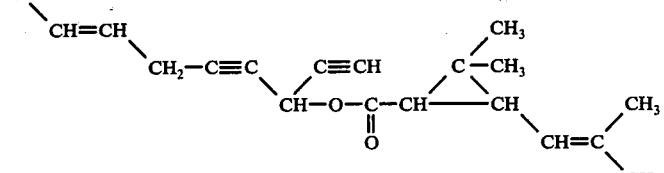<br>$n_D^{25}$: 1.5096 |

-continued

| No. | Name | Formula |
|---|---|---|
| 76 | 1-Ethynyl-4-phenyl-2-butyn-1-yl chrysanthemate | 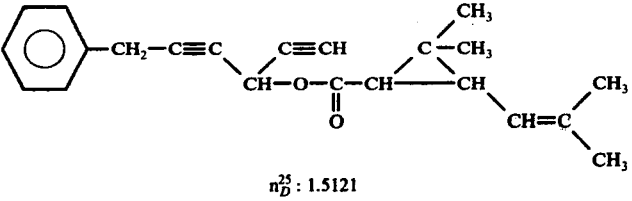 $n_D^{25}$: 1.5121 |
| 77 | 1-Ethynyl-5-phenyl-2-pentyn-1-yl chrysanthemate | 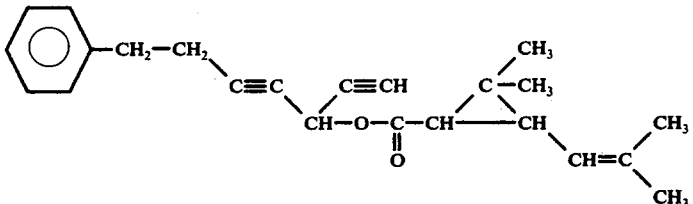 $n_D^{25}$: 1.5118 |
| 78 | 1-Ethynyl-6-phenyl-2-hexyn-1-yl chrysanthemate | 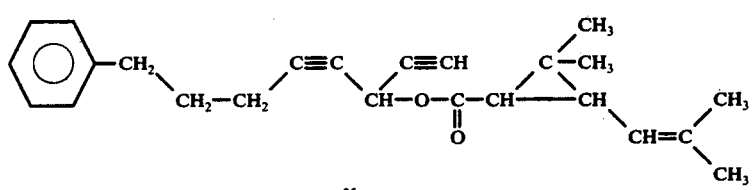 $n_D^{25}$: 1.5102 |
| 79 | 1-Ethynyl-4-phenoxy-2-butyn-1-yl chrysanthemate | 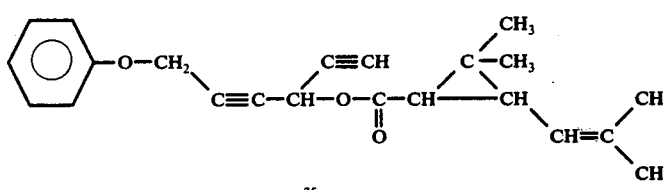 $n_D^{25}$: 1.5296 |
| 80 | 1-Ethynyl-4-phenylthio-2-butyn-1-yl chrysanthemate | 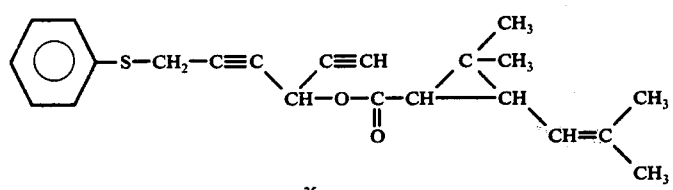 $n_D^{25}$: 1.5281 |
| 81 | 1-Ethynyl-3-phenyl-2-propyn-1-yl chrysanthemate | 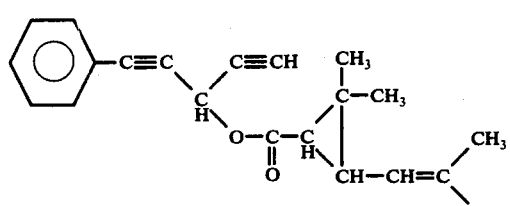 $n_D^{25}$: 1.5109 |
| 82 | 1-(1'-Propynyl)-5-hexen-2-yn-1-yl chrysanthemate | 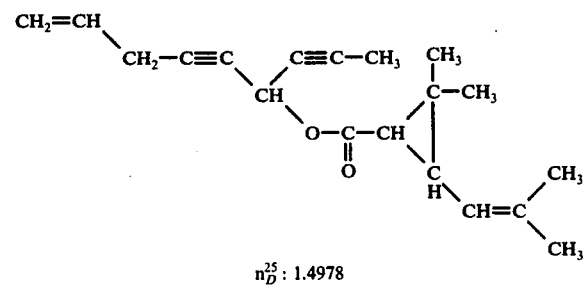 $n_D^{25}$: 1.4978 |

-continued

| No. | Name | Formula |
|-----|------|---------|
| 83 | 1-Ethynyl-4-(3',4'-methylene-dioxyphenyl)-2-butyn-1-yl chrysanthemate | $n_D^{25}$: 1.5108 |
| 84 | 1-Ethynyl-2-hexyn-1-yl 2',2',3',3'-tetramethyl-cyclopropanecarboxylate | $n_D^{25}$: 1.5048 |
| 85 | 1-Ethynyl-2-heptyn-1-yl 2',2',3',3'-tetramethylcyclo-propanecarboxylate | $n_D^{25}$ 1.5055 |
| 86 | 1-Ethynyl-5-hexen-2-yn-1-yl 2',2',3',3'-tetramethyl-cyclopropanecarboxylate | $n_D^{25}$: 1.5002 |
| 87 | 1-Ethynyl-4-phenyl-2-butyn-1-yl 2',2',3',3'-tetramethyl-cyclopropanecarboxylate | $n_D^{25}$: 1.5118 |
| 88 | 1-Ethynyl-4-phenoxy-2-butyn-1-yl 2',2',3',3'-tetramethyl-cyclopropanecarboxylate | $n_D^{25}$: 1.5207 |
| 89 | 1-Ethynyl-5-hexen-2-ynyl 2',2',3'-trimethylcyclo-propanecarboxylate | $n_D^{25}$: 1.5013 |

-continued

| No. | Name | Formula |
|---|---|---|
| 90 | 1-Ethynyl-5-hexen-2-ynyl 2',2'-dimethyl-3'-(2"-methyl-1",3"-butadienyl)cyclopropanecarboxylate | $n_D^{25}$: 1.4971 |
| 91 | 1-Ethynyl-5-hexen-2-ynyl 2',2'-dimethyl-3'-(1"-propenyl)cyclopropanecarboxylate | $n_D^{25}$: 1.4953 |
| 92 | 1-Ethynyl-5-hexen-2-ynyl 2',2'-dimethyl-3'-(1",3"-butadienyl)cyclopropanecarboxylate | $n_D^{25}$: 1.4968 |
| 93 | 1-Ethynyl-5-hexen-2-ynyl 2',2'-dimethylcyclopropanecarboxylate | $n_D^{25}$: 1.4922 |
| 94 | 1-Ethynyl-5-hexen-2-ynyl 2',2'-dimethyl-3'-cyclopentylidenemethylcyclopropanecarboxylate | $n_D^{25}$: 1.5034 |
| 95 | 1-Ethynyl-5-hexen-2-ynyl 2',2'-dimethyl-3'-(2",2"-dichorovinyl)cyclopropanecarboxylate | $n_D^{25}$: 1.5065 |

-continued

| No. | Name | Formula |
|---|---|---|
| 96 | 1-Ethynyl-5-hexen-2-ynyl 2',2'-dimethyl-3'-(2''-methoxycarbonyl-1''-propenyl)-cyclopropanecarboxylate | $n_D^{25}$: 1.5077 |
| 97 | 1-Ethynyl-5-hexen-2-ynyl 2',2'-dimethyl-3'-(2''-methoxymethyl-1''-propenyl)-cyclopropanecarboxylate | $n_D^{25}$ 1.5081 |
| 98 | 1-Ethynyl-5-hexen-2-ynyl 1',2',2',3',3'-pentamethyl-cyclopropanecarboxylate | $n_D^{25}$: 1.4998 |
| 99 | 1-Ethynyl-5-hexen-2-ynyl 1',2',2'-trimethyl-3'-(2''-methyl-1''-propenyl)cyclopropanecarboxylate | $n_D^{25}$: 1.4953 |
| 100 | 1-Ethynyl-5-hexen-2-ynyl 1',2',2'-trimethyl-3'-cyclopentylidenemethyl-cyclopropanecarboxylate | $n_D^{25}$: 1.5063 |
| 101 | 1-Ethynyl-5-hexen-2-ynyl 2',2'-dimethyl-3'-vinyl-cyclopropanecarboxylate | $n_D^{25}$: 1.5011 |

-continued

| No. | Name | Formula |
|---|---|---|
| 102 | 1-Ethynyl-3-(2'-cyclopentenyl)-allyl chrysanthemate | <br>$n_D^{25}$: 1.5021 |
| 103 | 1-Ethynyl-4-(1'-cyclopentenyl)-2-butenyl chrysanthemate | 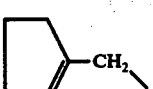<br>$n_D^{25}$: 1.5030 |
| 104 | 1-Ethynyl-2-methyl-3-(1'-cyclopentenyl)allyl 2'',2'',3'',3''-tetramethylcyclopropane-carboxylate | <br>$n_D^{25}$: 1.5078 |
| 105 | 1-Ethynyl-2-methyl-3-(2'-cyclopentenyl)allyl chrysanthemate | <br>$n_D^{25}$: 1.5066 |
| 106 | 1-Ethynyl-3-cyclopentylallyl chrysanthemate | <br>$n_D^{25}$: 1.4953 |
| 107 | 1-Ethynyl-3-(3'-cyclopentenyl)-allyl 2'',2''-dimethyl-3''-(1''',3'''-butadienyl)cyclopropanecarboxylate | <br>$n_D^{25}$: 1.5014 |

-continued

| No. | Name | Formula |
|---|---|---|
| 108 | 1-Ethynyl-2-ethyl-3-(1'-cyclopentenyl)allyl chrysanthemate | 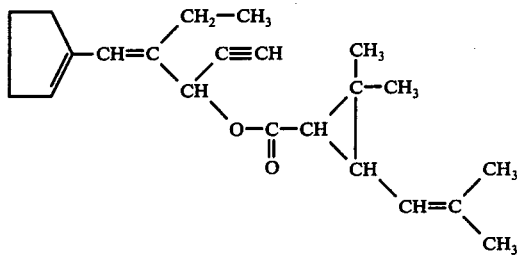<br>$n_D^{25}$: 1.5106 |
| 109 | 1-Ethynyl-2-ethyl-3-(2'-cyclopentenyl)allyl chrysanthemate | 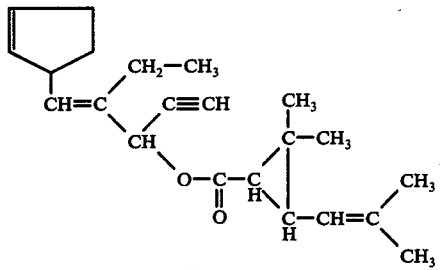<br>$n_D^{25}$: 1.5243 |
| 110 | 1-Ethynyl-2-methyl-3-(2'-cyclopentenyl)allyl 2'',2''-dimethyl-3''-(1'''-propenyl)-cyclopropanecarboxylate | 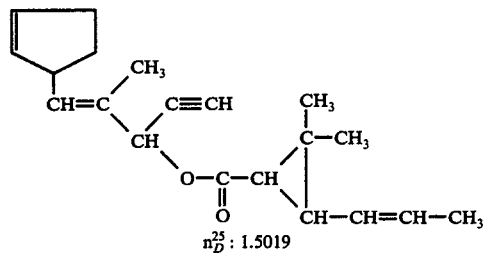<br>$n_D^{25}$: 1.5019 |
| 111 | 1-Ethynyl-2-methyl-4-(1'-cyclopentenyl)-2-butenyl 2'',2''-dimethyl-3''-cyclopentylidene-methylcyclopropanecarboxylate | 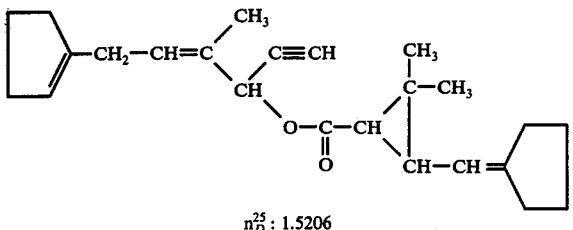<br>$n_D^{25}$: 1.5206 |
| 112 | 1-Ethynyl-4-(4'-oxa-1'-cyclopentenyl)-2-butenyl chrysanthemate | 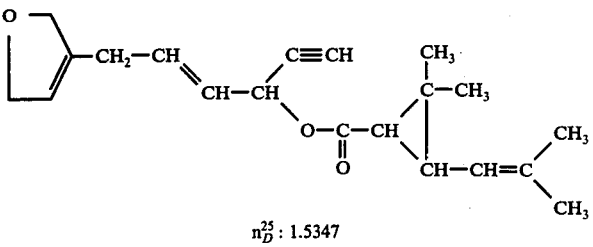<br>$n_D^{25}$: 1.5347 |
| 113 | 1-Ethynyl-2-methyl-3-cyclohexylallyl chrysanthemate | 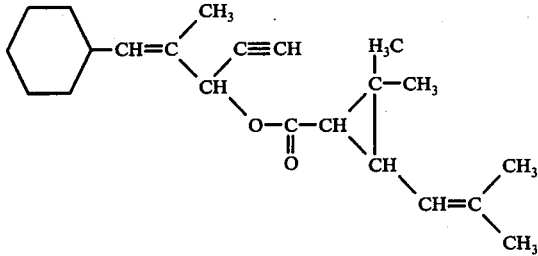<br>$n_D^{25}$: 1.4998 |

-continued

| No. | Name | Formula |
|---|---|---|
| 114 | 1-Ethynyl-2-methyl-3-(3'-cyclohexenyl)allyl chrysanthemate | $n_D^{25}$: 1.5079 |
| 115 | 1-Ethynyl-3-(3'-cyclohexenyl)allyl 2'',2''-dimethyl-3''-(1'''-propenyl)cyclopropanecarboxylate | $n_D^{25}$: 1.5004 |
| 116 | 1-Ethynyl-3-(2'-cyclohexenyl)allyl 2'',2'',3'',3''-tetramethylcyclopropanecarboxylate | $n_D^{25}$: 1.4911 |
| 117 | 1-Ethynyl-4-(1'-cyclohexenyl)-2-butenyl 2'',2'',3''-trimethylcyclopropanecarboxylate | $n_D^{25}$: 1.4938 |
| 118 | 1-Ethynyl-2-methyl-3-(3''-cyclohexenyl)allyl 2'',2''-dimethylcyclopropanecarboxylate | $n_D^{25}$: 1.4982 |

-continued

| No. | Name | Formula |
|-----|------|---------|
| 119 | 1-Ethynyl-2-methyl-4-(2'-cyclohexenyl)-2-butenyl chrysanthemate | 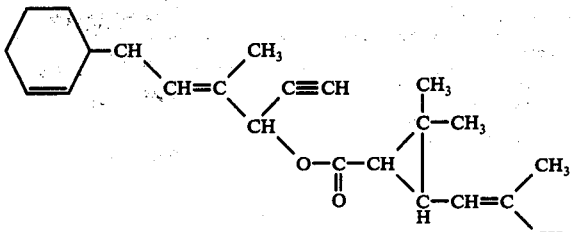<br>$n_D^{25}$: 1.5107 |
| 120 | 1-Ethynyl-3-(3'-cyclohexenyl)allyl 2'',2''-dimethyl-3''-(2''',2'''-dichlorovinyl)-cyclopropanecarboxylate | 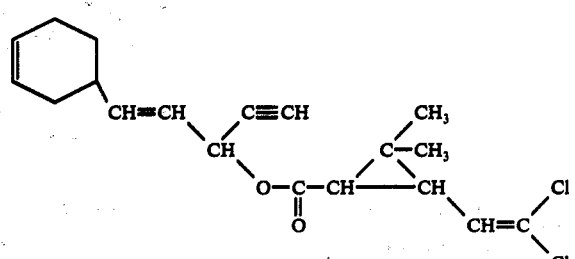<br>$n_D^{25}$: 1.5263 |
| 121 | 1-Ethynyl-2-methyl-3-(3'-cyclohexenyl)allyl 2'',2''-dimethyl-3''-cyclopentylidene-methylcyclopropanecarboxylate | 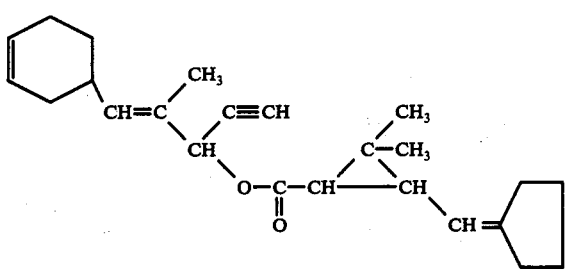<br>$n_D^{25}$: 1.5239 |
| 122 | 1-Ethynyl-2-methyl-3-(2'-oxa-3'-cyclohexenyl)allyl 2'',2''-dimethyl-3''-(1''',3'''-butadienyl)cyclopropane-carboxylate | 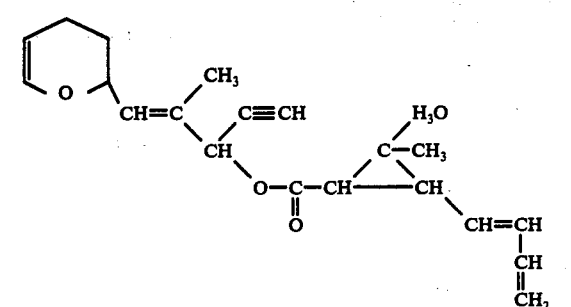<br>$n_D^{25}$: 1.5374 |
| 123 | 1-Ethynyl-3-(5'-oxa-3'-cyclohexenyl)allyl chrysanthemate | 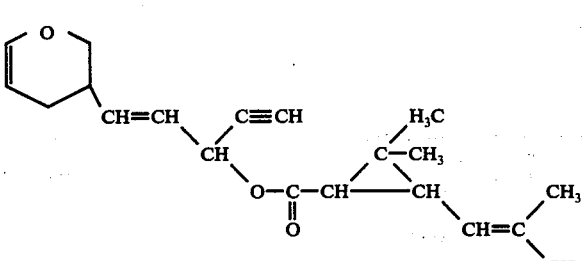<br>$n_D^{25}$: 1.5358 |

-continued

| No. | Name | Formula |
|-----|------|---------|
| 124 | 1-Ethynyl-2-ethyl-3-(2'-oxa-3'-cyclohexenyl)allyl 2'',2''-dimethyl-3''-(1'''-propenyl)-cyclopropanecarboxylate | 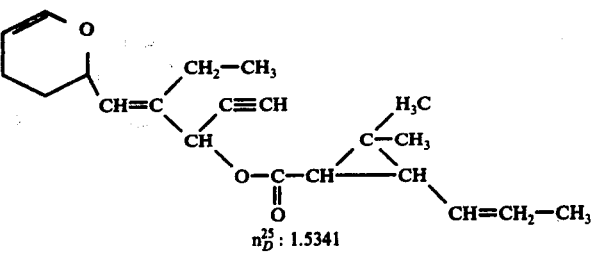  $n_D^{25}$: 1.5341 |
| 125 | 1-Ethynyl-2-methyl-3-(2'-oxacyclohexyl)allyl chrysanthemate | 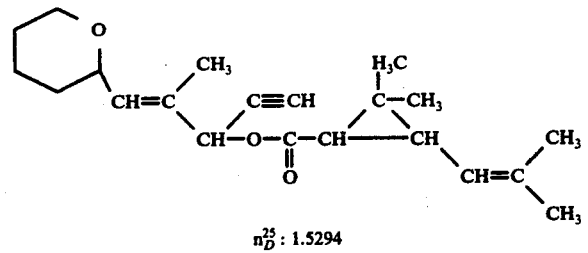  $n_D^{25}$: 1.5294 |
| 126 | 1-Ethynyl-2-methyl-2-pentenyl-2',2'-dimethyl-3'-(2'',2''-dichlorovinyl)cyclopropane-carboxylate | 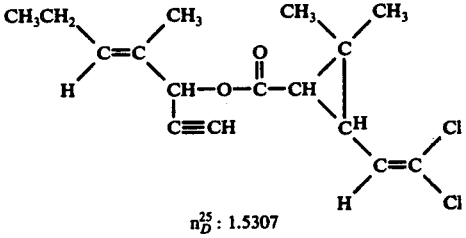  $n_D^{25}$: 1.5307 |
| 127 | 1-Ethynyl-2-methyl-2,5-hexadienyl 2',2'-dimethyl-3'-(2'',2''-dichlorovinyl) cyclopropane-carboxylate | 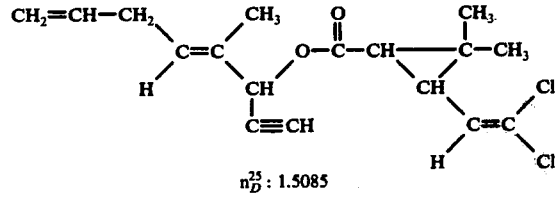  $n_D^{25}$: 1.5085 |
| 128 | 1-Ethynyl-2-methyl-2,6-heptadienyl chrysanthemate | 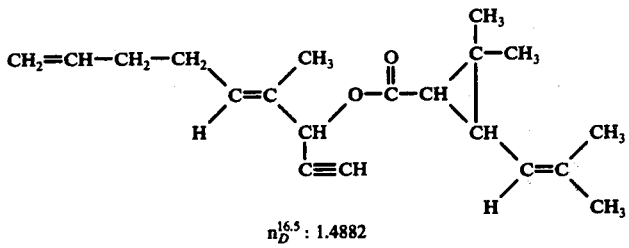  $n_D^{16.5}$: 1.4882 |
| 129 | 1-Ethynyl-2-methyl-2,6-heptadienyl 2',2'-dimethyl-3'-(2'',2''-dichlorovinyl)cyclo-propanecarboxylate | 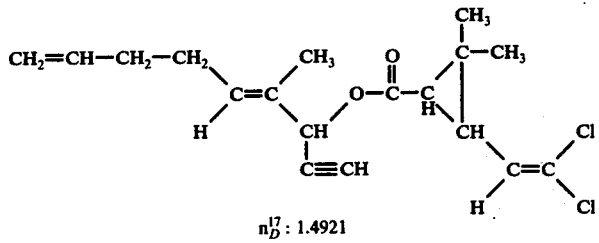  $n_D^{17}$: 1.4921 |
| 130 | 1-Ethynyl-2-methyl-2-butenyl 2',2'-dimethyl-3'(2'',2''-dichlorovinyl)cyclo-propanecarboxylate | 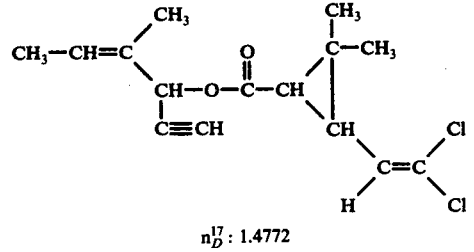  $n_D^{17}$: 1.4772 |

-continued

| No. | Name | Formula |
|---|---|---|
| 131 | α-Ethynyl-γ-benzylallyl 2′,2′-dimethyl-3′-(2″,2″-dichlorovinyl)cyclopropanecarboxylate | 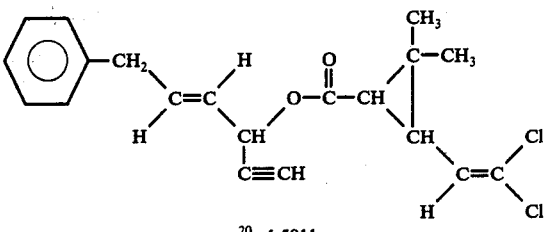<br>$n_D^{20}$ : 1.5011 |
| 132 | α-Ethynylcinnamyl 2′,2′-dimethyl-3′-(2″,2″-dichlorovinyl)cyclopropanecarboxylate | 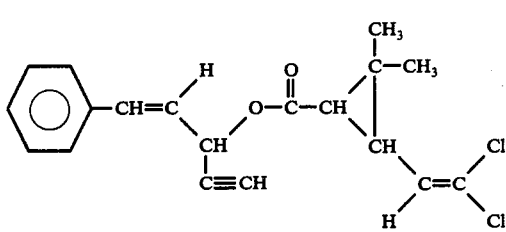<br>$n_D^{21.5}$ : 1.5034 |
| 133 | α-Ethynylcinnamyl 2′,2′-dimethyl-3′-cyclopentylidenemethyl-cyclopropanecarboxylate | 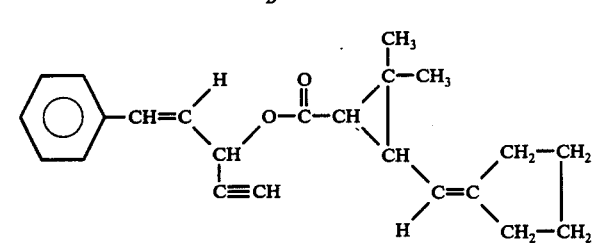<br>$n_D^{21.5}$ : 1.5121 |
| 134 | α-Ethynylcinnamyl 2′,2′-dimethyl-3′-(2″-methoxymethyl-1″-propenyl)cyclopropanecarboxylate | 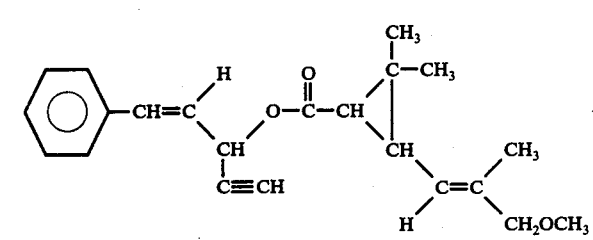<br>$n_D^{21.5}$ : 1.5022 |
| 135 | α-Ethynyl-β-bromocinnamyl 2′,2′-dimethyl -3′-(2″,2″-dichlorovinyl)cyclopropanecarboxylate | 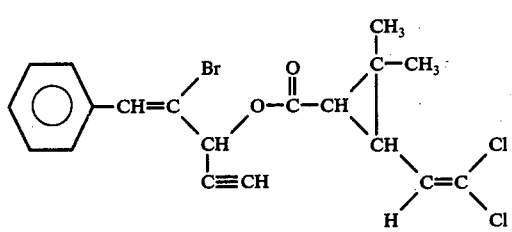<br>$n_D^{22}$ : 1.5008 |
| 136 | α-Ethynyl-β-methyl-2,6-dimethyl-4-methoxycinnamyl 2′,2′-dimethyl-3′-(2″,2″-dichlorovinyl)-cyclopropanecarboxylate | 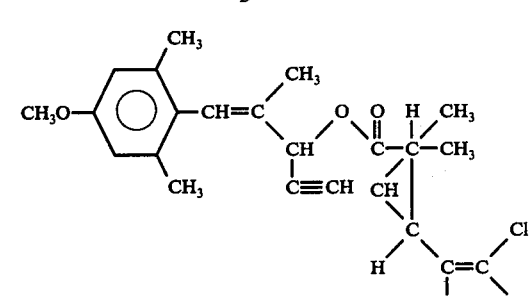<br>$n_D^{22}$ : 1.4997 |

-continued

| No. | Name | Formula |
|---|---|---|
| 137 | α-Ethynyl-β-methyl-4-cyano-cinnamyl 2',2'-dimethyl-3'-(2'',2''-dichlorovinyl)-cyclopropanecarboxylate | $n_D^{22}$: 1.5123 |
| 138 | α-Ethynyl-γ-phenylcinnamyl 2,2-dimethyl-3-(2',2'-dichlorovinyl)cyclopropane-carboxylate | $n_D^{21.5}$: 1.5003 |
| 139 | α-Ethynyl-β-methyl-3,4-methylenedioxycinnamyl 2',2'-dimethyl-3'-(2'',2''-dichloro-vinyl)cyclopropanecarboxylate | $n_D^{21.5}$: 1.4983 |
| 140 | α-Ethynyl-γ-(2-furyl)allyl 2',2'-dimethyl-3'-(2'',2''-dichlorovinyl)cyclopropane-carboxylate | $n_D^{20}$: 1.4975 |
| 141 | α-Ethynyl-β-ethylcinnamyl 2,2-dimethyl-3'-(2'',2''-dichlorovinyl)-cyclo-propanecarboxylate | $n_D^{20}$: 1.4935 |
| 142 | 1-Ethynyl-4-methoxy-2-butynyl 2',2'-dimethyl-3'-(2'',2''-dichlorovinyl) cyclopropane-carboxylate | $n_D^{20}$: 1.4955 |

-continued

| No. | Name | Formula |
|-----|------|---------|
| 143 | 1-Ethynyl-5-hexen-2-ynyl 2',2'-dimethyl-3'-(2'',2''-dichlorovinyl)-cyclopropanecarboxylate | |
| 144 | 1-Ethynyl-4-phenoxy-2-butynyl 2',2'-dimethyl-3'-(2'',2''-dichlorovinyl)-cyclopropanecarboxylate | $n_D^{21.5}$: 1.4990 |
| 145 | 1-Ethynyl-2-hexen-5-ynyl 2',2'-dimethyl-3'-(2'',2''-dichlorovinyl)cyclopropane-carboxylate | $n_D^{25}$: 1.5083 |
| 146 | 1-Ethynyl-2-methyl-2-hexen-5-ynyl chrysanthemate | $n_D^{25}$: 1.5099 |
| 147 | 1-Ethynyl-2-methyl-2-hexen-5-ynyl 2',2'-dimethyl-3'-(2'',2''-dichlorovinyl)-cyclopropanecarboxylate | $n_D^{25}$: 1.5045 |
| 148 | 1-Ethynyl-2-methyl-2-hepten-6-ynyl chrysanthemate | $n_D^{25}$: 1.4988 |
| 149 | 1-Ethynyl-2-methyl-2-hepten-6-ynyl 2',2'-dimethyl-3'-(2'',2''-dichlorovinyl)-cyclopropanecarboxylate | $n_D^{25}$: 1.4963 |

-continued

| No. | Name | Formula |
|---|---|---|
| 150 | 1-Ethynyl-2-hepten-6-ynyl chrysanthemate | $n_D^{25}$: 1.4951 |
| 151 | 1-Ethynyl-2-methyl-4-phenyl-2-butenyl 2',2'-dimethyl-3'-(2'',2''-dichlorovinyl)-cyclopropanecarboxylate | $n_D^{25}$: 1.5121 |
| 152 | 1-Ethynyl-2-methyl-4-phenyl-2-butenyl chrysanthemate | $n_D^{25}$: 1.5135 |
| 153 | 1-Ethynyl-2,5-hexadienyl chrysanthemate | $n_D^{25}$: 1.4899 |
| 154 | 1-Ethynyl-2,6-heptadienyl chrysthemate | $n_D^{25}$: 1.4832 |
| 155 | 1-Ethynyl-4-ethylthio-2-butynyl chrysanthemate | $n_D^{25}$: 1.5315 |
| 156 | 1-Ethynyl-5-methylthio-2-pentynyl chrysanthemate | $n_D^{25}$: 1.5476 |

| No. | Name | Formula |
|---|---|---|
| 157 | 1-Ethynyl-4-(2'-furyl)-2-butenyl chrysanthemate | 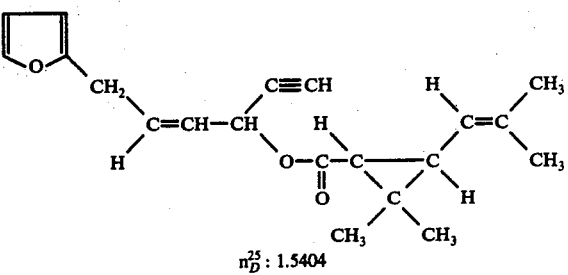 $n_D^{25}$: 1.5404 |
| 158 | 1-Ethynyl-4-(2'-thienyl)-2-butenyl chrysanthemate | 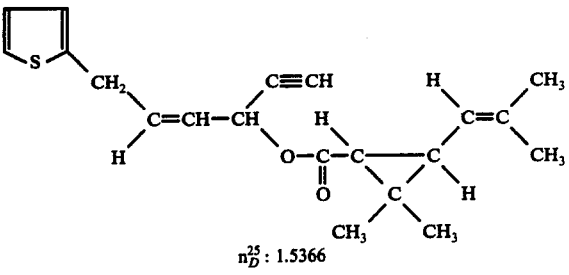 $n_D^{25}$: 1.5366 |
| 159 | 1-Ethynyl-4-(4'-oxacyclopentyl)-2-butenyl chrysanthemate | 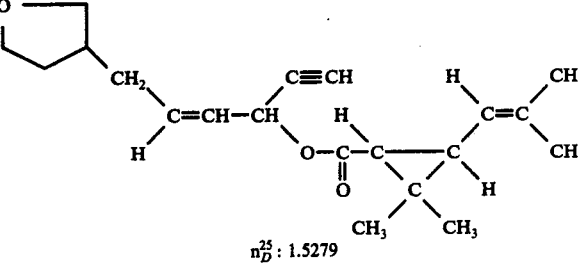 $n_D^{25}$: 1.5279 |
| 160 | 1-Ethynyl-4-cyclohexyl-2-butenyl chrysanthemate | 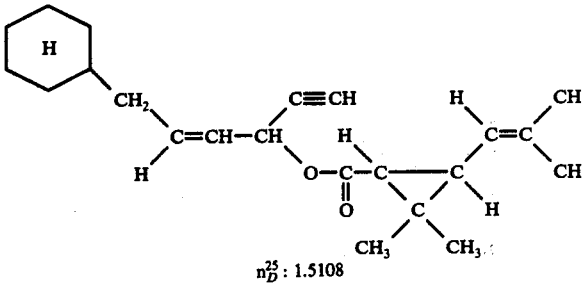 $n_D^{25}$: 1.5108 |

The esters represented by the aforesaid formula (I) can be obtained by reacting an alcohol, its halide or arylsulfonate, of the formula (II),

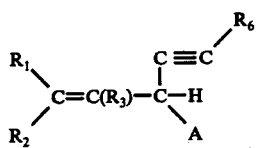

wherein $R_1$, $R_2$, $R_3$ and $R_5$ are as defined above; and A is a hydroxy group, a halogen atom or an arylsulfoxy group, with a cyclopropanecarboxylic acid, or its reactive derivative, of the formula (III),

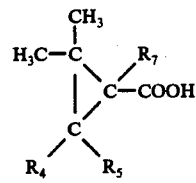

wherein $R_4$, $R_5$ and $R_7$ are as defined above, if necessary, in the presence of a suitable reaction auxiliary reagent.

The reactive derivative of cyclopropanecarboxylic acid which is referred to herein includes acid halides, acid anhydrides, lower alkyl esters or salts.

Procedures for synthesizing the esters according to the present invention are explained in more detail below.

In case an alcohol of the formula (II) (A is a hydroxy group) and a carboxylic acid of the formula (III) are used, the reaction is carried out under dehydration conditions. Thus, the alcohol is reacted at room temperature or at an elevated temperature with the carboxylic acid in a suitable inert solvent in the presence of a dehydrating agent such as dicyclohexylcarbodiimide, whereby a desired ester can be obtained in a high yield.

In case an acid halide is used as a reactive derivative of the carboxylic acid of the general formula (III), the reaction can be sufficiently accomplished at room temperature by reacting the acid halide with an alcohol of the formula (II) (A is a hydroxy group), using as a halogen halide-removing reagent such an organic tertiary base as pyridine, triethylamine or the like. The acid halide used in this case may be any of the halides within the scope of the present invention, but is ordinarily an acid chloride. In the reaction, the use of a solvent is desirable for smooth progress of the reaction, and such an inert solvent as benzene, toluene or petroleum benzine is ordinarily used.

In case an acid anhydride is used as a reactive derivative of the carboxylic acid of the formula (III), no auxiliary agent is particularly required, and the object can be accomplished by reacting the acid anhydride with an alcohol of the formula (II) (A is a hydroxy group). In this case, the elevation of temperature is preferably for acceleration of the reaction, and the use of an inert solvent such as toluene or xylene is preferable for smooth progress of the reaction, though not always indispensable.

In case a lower alkyl ester is used as a reactive derivative of the carboxylic acid of the formula (III), the reaction is accomplished by reacting said ester with an alcohol of the formula (II) (A is a hydroxy group) at an elevated temperature in the presence of such a basic catalyst as sodium alkoxide, while removing out of the system a low boiling alcohol formed in the reaction. The use of such an inert solvent as benzene, toluene or the like is preferable for smooth progress of the reaction. The lower alkyl ester of carboxylic acid used in this case is preferably methyl ester, ethyl ester, n-propyl ester, isopropyl ester or n-butyl ester.

In case an ester of the formula (I) is desired to be obtained by use of a halide of the alcohol of the formula (II) (A is a halide), the carboxylic acid or the formula (III), which is the other reactant, may be used in the form of an alkali metal salt or a salt of an organic tertiary base, or an organic tertiary base may be added, at the time of reaction, together with the carboxylic acid. In this case, it is desirable for smooth progress of the reaction that an inert solvent such as benzene or acetone is used and the system is heated to the boiling point of the solvent or to a temperature near the boiling point thereof. The halide of alcohol used in the above case is ordinarily in the form of chloride, but may be any other halide such as bromide or the like.

In the case where an ester of the formula (I) is desired to be obtained by use of an arylsulfonate of the alcohol of the formula (II), the other reactant and the reaction conditions are the same as in the case where the above-mentioned halide of alcohol is used. As the arylsulfonate, a tosylate is frequently used, in general.

The present invention will be more particularly illustrated by the following Examples which should not restrict the invention defined in the attached claims.

Production of the Esters Represented by the Formula (I)

The esters shown in Table 1 were produced by standard processes each represented by A, B, C, D, E and F as follows:

Process A

A Reaction of an Alcohol with a Carboxylic Acid Halide 0.05 Mol of an alcohol was dissolved in three times the volume of dry benzene. 0.075 Mol of pyridine was added to the solution. On the other hand, 0.053 mol of a carboxylic acid chloride was dissolved in three times the volume of dry benzene. The solution thus obtained was added at a time to the above-mentioned solution, whereupon an exothermic reaction occurred. After the solution had been allowed to stand overnight in a tightly sealed vessel, a small amount of water was added to dissolve pyridine hydrochloride precipitated. The aqueous layer was separated and the organic layer was then washed with 5% aqueous hydrochloric acid, a saturated aqueous solution of sodium bicarbonate and a saturated aqueous salt solution successively. After the organic layer had been dried on anhydrous sodium sulfate, the benzene solution was stirred with neutral alumina for 30 minutes to decolorize and filtered off, and then the benzene was removed by distillation to obtain the final product.

Process B

A Reaction (Dehydration) between an Alcohol and a Carboxylic Acid

A solution of 0.05 mol of an alcohol in three times the volume of benzene was mixed with a solution of 0.05 mol of a carboxylic acid in three times the volume of benzene. 0.08 Mol of dicyclohexylcarbodiimide was added thereto. After the mixture had been allowed to stand overnight in a tightly sealed vessel, the mixture was refluxed for two hours to complete the reaction and then cooled. After dicyclohexylcarbodiimidourea precipitated was filtered off, the same after-treatment as in the standard operational method A was then carried out to obtain the final product.

Process C

A Reaction of an Alcohol with a Carboxylic Acid Anhydride.

0.05 Mol of an alcohol was dissolved in three times the volume of toluene. 0.05 Mol of a carboxylic acid anhydride synthesized from the corresponding carboxylic acid and acetic anhydride was added thereto. The mixture was then reacted for three hours at 100° C. The reaction mixture was cooled and a 5% aqueous solution of sodium hydroxide was added to neutralize the mixture. Excess of the acid anhydride and the carboxylic acid formed by the reaction were recovered in the form of sodium salt. The after-treatment of the organic layer was then carried out in the same manner as in the standard operational method A to obtain the desired ester.

Process D

A Transesterification between an Alcohol and a Lower Alkyl Carboxylate 0.05 Mol of an alcohol and 0.06 mol of an ethyl carboxylate were dissolved in five times the volume of dry toluene. 2 Grams of sodium ethoxide was added. The mixture was then refluxed with well stirring for 10 hours to complete the reaction. Cold water was carefully added and the mixture was separated into an aqueous layer and an organic layer. The after-treatment was then carried out in the same manner as in the standard operational method A to obtain the final product.

Process E

A Reaction of a Halide Compound with a Carboxylic Acid 0.05 Mol of a halide compound and 0.06 mol of a carboxylic acid were dissolved in three times the volume of acetone. The solution was warmed at 15° to 20° C. A solution of 0.08 mol of triethylamine in three times the volume of acetone was dropped into the above solution with stirring in one hour. The mixture was then refluxed for two hours to complete the reaction. After the reaction mixture had been cooled, the triethylamine hydrochloride separated was filtered off and the acetone was removed from the filtrate by distillation. Three times the volume of benzene was added to the remaining liquid and the after-treatment of the liquid was carried out in the same manner as in the standard operational method A to obtain the desired ester.

Process F

A Reaction of the Arylsulfonate of an Alcohol with a Carboxylate 0.05 Mol of an arylsulfonate was dissolved in three times the volume of acetone. 0.06 Mol of sodium carboxylate, synthesized by reaction the corresponding carboxylic acid with an equimolar amount of sodium hydroxide in water and distilling off the water and evaporating the residue to dryness, was added at room temperature with well stirring in 30 minutes. The mixture was then refluxed for 30 minutes to complete the reaction. After the mixture had been cooled, the solid matter separated was removed by filtration and the acetone was removed from the filtrate by distillation. The residue was dissolved in three times the volume of benzene. The after-treatment of the solution was then carried out in the same manner as in the standard operational method A to obtain the final product.

Typical examples of cyclopropanecarboxylic acids of the formula (III) which are used in the present invention are as shown below, which include cis and trans isomers and optically active acids according to double bond and/or assymetric carbon atoms.

And reactive derivatives of these carboxylic acids are easily prepared from the corresponding carboxylic acid by such a known method as used for chrysanthemic acid.

2,2-Dimethyl-cyclopropanecarboxylic acid 2,2,3-Trimethyl-cyclopropanecarboxylic acid
2,2,3,3-Tetramethyl-cyclopropanecarboxylic acid
2,2-Dimethyl-3-(2'-methyl-1'-propenyl)-cyclopropanecarboxylic acid
2,2-Dimethyl-3-vinyl-cyclopropanecarboxylic acid
2,2-Dimethyl-3-(1'-propenyl)cyclopropanecarboxylic acid
2,2-Dimethyl-3-(1',3'-butadienyl)cyclopropanecarboxylic acid
2,2-Dimethyl-3-(2'-methyl-1',3'-butadienyl)cyclopropanecarboxylic acid
2,2-Dimethyl-3-(2',2'-dichlorovinyl)cyclopropanecarboxylic acid
2,2-Dimethyl-3-cyclopentylidenemethyl-cyclopropanecarboxylic acid
2,2-Dimethyl-3-(2'-methoxycarbonyl-1'-propenyl)-cyclopropanecarboxylic acid
2,2-Dimethyl-3-(2'-methoxymethyl-1'-propenyl)-cyclopropanecarboxylic acid
1,2,2,3,3-Pentamethyl-cyclopropanecarboxylic acid
1,2,2-Trimethyl-3-(2'-methyl-1'-propenyl)-cyclopropanecarboxylic acid
1,2,2-Trimethyl-3-(2'-methoxycarbonyl-1'-propenyl)-cyclopropanecarboxylic acid
1,2,2-Trimethyl-3-cyclopentylidenemethylcyclopropanecarboxylic acid Typical examples of α-alkynyl alcohols of the formula (II) which are used in the present invention are as shown below.

Halides are prepared by halogenating the alcohols with thionyl halides or phosphorus halides, and arylsulfonates prepared by treating alcohols with arylsulfochloride.

1-Ethynyl-2-butenyl alcohol
1-Ethynyl-2-methyl-2-butenyl alcohol
1-Ethynyl-3-methyl-2-butenyl alcohol
1-Ethynyl-2-methyl-2-pentenyl alcohol
1-Ethynyl-2-ethyl-2-hexenyl alcohol
1-Ethynyl-2,5-hexadienyl alcohol
1-Ethynyl-2-methyl-2,5-hexadienyl alcohol
1-Ethynyl-2-isopropyl-allyl alcohol
1-(1'-Propynyl)-2-methyl-2-butenyl alcohol
1-Ethynyl-1-(1'-cyclohexenyl)methyl alcohol
1-Ethynyl-1-(1'-cyclopentenyl)methyl alcohol
1-Ethynyl-1-cyclohexylidenemethyl alcohol
1-Ethynyl-3-propargyl-allyl alcohol
1-Ethynyl-2-methylpropargyl-allyl alcohol
1-Ethynyl-2,6-heptadienyl alcohol
α-Ethynyl-cinnamyl alcohol
α-Ethynyl-β-methylcinnamyl alcohol
α-Ethynyl-β-methyl-4-methylcinnamyl alcohol
α-Ethynyl-β-methyl-2-chlorocinnamyl alcohol
α-Ethynyl-β-methyl-3,4-methylenedioxycinnamyl alcohol
α-Ethynyl-β-methyl-3-nitrocinnamyl alcohol
α-Ethynyl-β-methyl-4-dimethylaminocinnamyl alcohol
α-Ethynyl-β-methyl-4-cyanocinnamyl alcohol
α-Ethynyl-β-methyl-4-isopropylcinnamyl alcohol
α-Ethynyl-β-ethyl-4-ethoxycinnamyl alcohol
α-Ethynyl-β-methyl-3,4-dimethoxycinnamyl alcohol
α-Ethynyl-β-methyl-2,6-dimethyl-4-methoxycinnamyl alcohol
1-Ethynyl-4-ethylthio-2-butynyl alcohol
1-Ethynyl-5-methylthio-2-pentynyl alcohol
1-Ethynyl-4-(2'-furyl)-2-butenyl alcohol
1-Ethynyl-4-(2'-thenyl)-2-butenyl alcohol
α-Ethynyl-β-bromocinnamyl alcohol
α-Ethynyl-β-vinylcinnamyl alcohol
α-Ethynyl-β-isopropylcinnamyl alcohol
α-Ethynyl-β-propargylcinnamyl alcohol
α-Ethynyl-β-phenylcinnamyl alcohol
α-Ethynyl-β-benzylcinnamyl alcohol
α-Ethynyl-γ-phenylcinnamyl alcohol
α-Ethynyl-γ-methylcinnamyl alcohol
α-(1-Propynyl)-β-methylcinnamyl alcohol
α-Ethynyl-γ-(2-furyl)allyl alcohol
α-Ethynyl-γ-(2-thienyl)allyl alcohol
α-Ethynyl-γ-benzylallyl alcohol
1-Ethynyl-2-butyn-1-ol
1-Ethynyl-2-pentyn-1-ol
1-Ethynyl-2-hexyn-1-ol 1-Ethynyl-2-heptyn-1-ol
1-Ethynyl-4-methoxy-2-butyn-1-ol
1-Ethynyl-5-methoxy-2-pentyn-1-ol
1-Ethynyl-4-ethoxy-2-butyn-1-ol
1-Ethynylhexa-2-yn-5-en-1-ol
1-Ethynylhexa-2,5-diyn-1-ol
1-Ethynylhepta-2-yn-6-en-1-ol
1-Ethynylhepta-2,6-diyn-1-ol
1-Ethynyl-6-chloro-2-yn-5-en-1-ol
1-Ethnyl-4-phenyl-2-butyn-1-ol
1-Ethynyl-5-phenyl-2-pentyn-1-ol
1-Ethynyl-6-phenyl-2-hexyn-1-ol
1-Ethynyl-4-phenylthio-2-butyn-1-ol
1-Ethynyl-3-(3'-methylphenyl)-2-propyn-1-ol
1-(1'-Propynyl)-4-(3'',4''-methylenedioxyphenyl)-2-butyn-1-ol
1-Ethnyl-4-(3'-tetrahydrofuryl)-2-butenyl alcohol
1-Ethnyl-4-cyclohexyl-2-butenyl alcohol
1-Ethynyl-4-phenoxy-2-butynyl alcohol
1-Ethynyl-3-(2'-cyclopentenyl)allyl alcohol
1-Ethnyl-2-methyl-3-(1'-cyclopentenyl)allyl alcohol
1-Ethynyl-3-cyclopentylallyl alcohol
1-Ethnyl-2-ethyl-3-(1'-cyclopentenyl)allyl alcohol
1-Ethnyl-2-methyl-3-(2'-cyclopentenyl)allyl alcohol
1-Ethnyl-4-(1'-cyclopentenyl)-2-butenyl alcohol
1-Ethnyl-3-(3'-cyclopentenyl)allyl alcohol
1-Ethnyl-2-methyl-4-(1'-cyclopentenyl)-2-butenyl alcohol
1-Ethynyl-4-(4'-oxa-1'-cyclopentenyl)-2-butenyl alcohol
1-Ethnyl-2-methyl-3-cyclohexylallyl alcohol
1-Ethnyl-3-(3'-cyclohexenyl)allyl alcohol
1-Ethnyl-4-(1'-cyclohexenyl)-2-butenyl alcohol
1-Ethnyl-4-(2'-cyclohexenyl)-2-butenyl alcohol
1-Ethynyl-2-methyl-3-(3'-cyclohexenyl)allyl alcohol
1-Ethnyl-4-cyclopentyl-2-butenyl alcohol
1-Ethnyl-3-(2'-cyclohexenyl)allyl alcohol
1-Ethnyl-2-methyl-3-(2'-oxa-3'-cyclohexenyl)allyl alcohol
1-Ethnyl-3-(5'-oxa-3'-cyclohexenyl)allyl alcohol
1-Ethnyl-2-ethyl-3-(2'-oxa-3'-cyclohexenyl)allyl alcohol
1-Ethnyl-2-methyl-3-(2'-oxacyclohexyl)allyl alcohol The alkynyl alcohol represented by the formula (II) is a novel compound, and may be prepared easily according to the following processes.

The processes which comprise reacting an aldehyde compound represented by the formula (IV) with the ethynyl compound represented by the formula (V) or a Grignard regent represented by the formula (VI) are as follows:

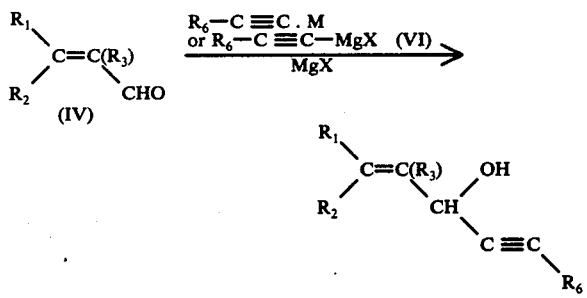

wherein $R_1$, $R_2$, $R_3$ and $R_6$ are as defined above, M represents an alkali metal (ex. lithium, sodium, potassium) and X represents a chlorine or a bromine atom.

Of the above-mentioned starting materials, the compound represented by the formula (IV) may be prepared easily according to the following processes;

(1) The process which comprises reacting a carbonyl compound of the formula (VII),

(VII)

wherein $R_1$ and $R_2$ are as defined above, with an aldehyde compound of the formula (VIII), $$R_3—CH_2—CHO \quad (VIII)$$

wherein $R_3$ is as defined above, by aldol condensation reaction.

(2) The process which comprises reducing α,β-unsaturated ester of the formula (IX),

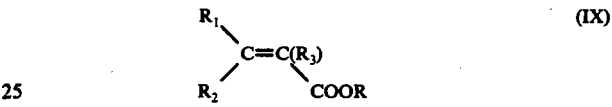

(IX)

wherein $R_1$, $R_2$ and $R_3$ are as defined above, and R is lower alkyl having up to 5 carbon atoms, or (3) The process which comprises reducing an alcohol compound of the formula (X), $$R_1—C≡C—CH_2OH \quad (X)$$

wherein $R_1$ is as defined above with lithium alminium hydride to form the alcohol of the formula (XI),

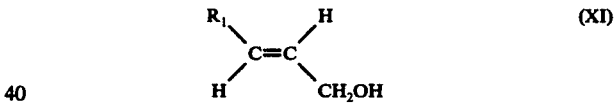

(XI)

and further oxidizing the said alcohol compound (XI).

On the other hand, the starting material of the formula (IV) may be prepared easily according to the following process:

The process which comprises oxidizing an alcohol compound of the formula (X), $$R_1—C≡C—CH_2OH \quad (X)$$

wherein $R_1$ is as defined above.

Practical embodiments for preparing the starting materials are illustratively shown in the following reference examples, but are not limited thereto.

Reference Example 1

To a solution of ethynyl magnesium bromide (prepared from 2.91 g of magnesium) in 100 ml of tetrahydrofuran, was added dropwise 9.8 g of 2-methyl-2-pentenal at a temperature from 0° C to 10° C under cooling with ice-bath. The resulting reaction solution was stirred for 3 hours at room temperature to complete the reaction and then the reaction solution was poured into a saturated ammonium cloride solution with 50 g of ice. After stirring, the solution was extracted twice with 100 ml of ether and the organic layers were combined, and then washed with 50 ml of a saturated sodium chloride solution. After the organic layer had been dried over anhydrous sodium sulfate, the ether was evaporated. The remaining liquid was purified by distillation at reduced pressure to obtain 10.2 g of a colorless oily 1-ethynyl-2-methyl-2-pentenyl alcohol, b.p. 85°-88° C/20 mmHg.

Reference Example 2

To a solution of ethynyl magnesium bromide (prepared from 2.91 g of magnesium) in 100 ml of tetrahydrofuran, was added dropwise 11.0 g of 2-methyl-2,5-hexadienal at a temperature from 0° C to 10° C under cooling with ice-bath. The resulting reaction solution was stirred for 3 hours to complete the reaction and the same after-treatment as in the Reference Example 1 was then carried out to obtain 12.3 g of a colorless oily 1-ethynyl-2-methyl-2,5-hexadienyl alcohol, b.p. 60°-65° C/7 mmHg.

The esters of the present invention find broad uses for the prevention of epidemics and for the control of insects injurious to stored cereals. Furthermore, they are extremely useful for the control of agricultural and forestry injurious insects such as green rice leaf-hoppers, smaller brown planthoppers, rice stem borers, larvae of Japanese giant silk moth, common cabbageworms, cabbage army worms, diamond back moth, cutworms, tent catapillar, etc. Particularly, they are low toxic and harmless to mammals, and hence are freely applicable to crops before harvest, food and packaging materials, and are usable for control of insects injurious to stored cereals and for home horticulture and green house cultivation.

The cyclopropanecarboxylic acid esters of the formula (I), which are exemplified by the above-mentioned compounds, are more excellent in insecticidal effect and knock-down effect than the known chrysanthemic acid esters. In order to make the above fact clearer, comparison in effectiveness between typical compounds of the present invention and allethrin is shown below with reference to Test Examples. Other compounds of the formula (I) and their geometrical isomers and optical isomers display excellent effects as well.

Test Example 1

0.6% Mosquito coils of the present compounds, compounds of U.S. Pat. No. b 3,862,174, U.S. Pat. No. 3,795,696, "Farkaš et al; Chem. listy", 52 688-94 (1958) and German Offenlegungsschrift No. 2,326,077, and allethrin were prepared in a similar manner as in Examples P, Q or R.

Into a $(70 cm)^3$ glass chamber were liberated 20 adults per group of houseflies. 1 Gram of each of the mosquito coils, was ignited on both ends and placed at the center of the chamber. Thereafter, the number of knocked down insects was counted to calculate 50% knockdown times ($KT_{50}$).

The results obtained from several repetition were as shown in Table 2 below.

Table 2

| Test Compound (0.6 % mosquito coil) | | $KT_{50}$ (min. sec.) Housefly |
|---|---|---|
| The present compound | 1 | 8'00" |
| " | 2 | 7'42" |
| " | 4 | 7'00" |
| " | 6 | 7'24" |
| " | 9 | 11'00" |
| " | 11 | 6'36" |
| " | 12 | 6'24" |
| " | 14 | 6'54" |
| " | 20 | 7'06" |
| " | 21 | 5'00" |
| " | 29 | 5'00" |
| " | 30 | 4'06" |
| " | 31 | 10'00" |
| " | 36 | 10'12" |
| " | 39 | 10'06" |
| " | 45 | 10'42" |
| " | 49 | 10'48" |
| " | 54 | 11'48" |
| " | 60 | 9'36" |
| " | 68 | 9'48" |
| " | 71 | 7'00" |
| " | 72 | 7'36" |
| " | 79 | 11'18" |
| " | 86 | 5'30" |
| " | 88 | 10'30" |
| " | 89 | 5'54" |
| " | 90 | 5'06" |
| " | 91 | 5'24" |
| " | 92 | 5'00" |
| " | 104 | 12'18" |
| " | 111 | 12'00" |
| " | 114 | 11'36" |
| " | 121 | 11'48" |
| " | 122 | 11'12" |
| " | 126 | 4'18" |
| " | 127 | 4'12" |
| " | 128 | 6'06" |
| " | 131 | 12'24" |
| " | 134 | 8'54" |
| " | 143 | 7'06" |
| " | 146 | 6'30" |
| " | 147 | 4'00" |
| " | 151 | 8'54" |
| " | 153 | 9'00" |
| " | 154 | 9'30" |
| " | 158 | 12'06" |

Table 2-continued

| Test Compound (0.6 % mosquito coil) | KT$_{50}$ (min. sec.) Housefly |
|---|---|
| Compounds of U.S. Pat. No. 3,862,174: | |
| CH≡C—CH$_2$—(furan)—CH(C≡CH)—O—CO—CH—C(CH$_3$)(CH$_3$)—CH—CH=C(CH$_2$OCH$_3$)(CH$_3$) | 22'42" |
| C$_6$H$_5$—CH$_2$—(furan)—CH(C≡CH)—O—CO—CH—C(CH$_3$)(CH$_3$)—CH—CH=C(CH$_2$OCH$_3$)(CH$_3$) | 25'00" |
| C$_6$H$_5$—O—(C$_6$H$_4$)—CH(C≡CH)—O—CO—CH—C(CH$_3$)(CH$_3$)—CH—CH=C(COCH$_3$)(CH$_3$) | 26'30" |
| CH≡C—CH$_2$—(furan)—CH(C≡CH)—O—CO—CH—C(CH$_3$)(CH$_3$)—CH—CH=(cyclopentanone) | 20'00" |
| C$_6$H$_5$—CH$_2$—C(Cl)=CH—CH(C≡CH)—O—CO—CH—C(CH$_3$)(CH$_3$)—CH—CH=C(CH$_2$OCH$_3$)(CH$_3$) | 27'00" |
| (thiophene)—CH$_2$—C(Cl)=CH—CH(C≡CH)—O—CO—CH—C(CH$_3$)(CH$_3$)—CH—CH=C(CH$_2$OCH$_3$)(CH$_3$) | 27'18" |
| Compounds of U.S. Pat. No. 3,795,696: | |
| HC≡C—CH$_2$—(2,6-dimethylphenyl)—CH$_2$—O—CO—CH—C(CH$_3$)(CH$_3$)—C(CH$_3$)(CH$_3$) | 13'18" |
| H$_3$C—C≡C—CH$_2$—(C$_6$H$_4$)—CH$_2$—O—CO—CH—C(CH$_3$)(CH$_3$)—C(CH$_3$)(CH$_3$) | 20'24" |
| Compound of "Farkaš et al; Chem. listy, 52 688-94 (1958)": | |
| CH$_2$=CH—CH$_2$—(2-methyl-4-oxocyclopentenyl)—O—CO—CH—C(CH$_3$)(CH$_3$)—CH—CH=CCl$_2$ | 24'30" |

Table 2-continued

| Test Compound (0.6 % mosquito coil) | KT$_{50}$ (min. sec.) Housefly |
|---|---|
| Compound of German Ofenlegungsschrift No. 2,326,077: [structure: benzyl-furan-CH$_2$-OC(O)-CH-CH(C(CH$_3$)$_2$)-CH=CCl$_2$] | 23'48" |
| Allethrin | 17'00" |

Test Example 2

A solution of 100 mg of each of the present compounds, compounds of U.S. Pat. No. 3,862,174, U.S. Pat. No. 3,795,696, U.S. Pat. No. 3,567,740, "Farkaš et al; Chem. listy, 52 688-94 (1958)", German Offenlegungsschrift No. 2,326,077 and allethrin in 1 ml of acetone was poured into a Petri dish of 9 cm in diameter to be air-dried. The dish was placed on the central part of bottom of a (70 cm)$^3$ glass chamber in a laboratory at 25° C to allow it to stand still for 20 hours for effecting non-heating fumigation. After removing the Petri dish, about 20 housefly adults were liberated in the chamber and knocked down houseflies with the lapse of time were observed to obtain KT$_{50}$ (50% knock-down time) value. The knocked down houseflies were collected, transferred to an observation cage and fed. After one day, the alive and dead were observed to obtain a mortality.

The results obtained were as shown in Table 3 below.

Table 3

| Test compound | | Housefly KT$_{50}$ (min.) | Mortality (%) |
|---|---|---|---|
| The present compound | 4 | 5.8 | 100 |
| " | 86 | 4.2 | 100 |
| " | 90 | 5.3 | 100 |
| " | 126 | 10.5 | 100 |
| " | 127 | 7.3 | 100 |
| " | 147 | 6.4 | 100 |
| Compounds of U.S. Pat. No. 3,862,174: [structure 1] | | >30 | 0 |
| [structure 2] | | >30 | 0 |
| [structure 3] | | >30 | 0 |
| [structure 4] | | >30 | 0 |
| [structure 5] | | >30 | 0 |

Table 3-continued

| Test compound | Housefly | |
|---|---|---|
| | KT$_{50}$ (min.) | Mortality (%) |
| 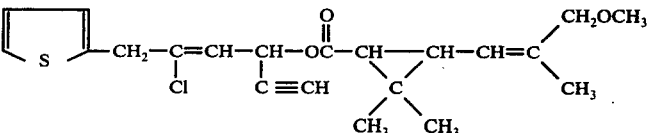 | >30 | 0 |
| Compounds of U.S. Pat. No. 3,795,696: | | |
| 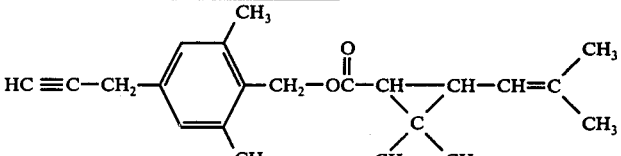 | >30 | 0 |
| 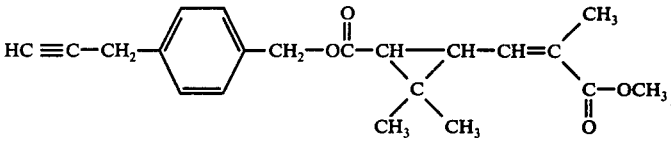 | >30 | 0 |
| Compound of U.S. Pat. No. 3,567,740: | | |
| 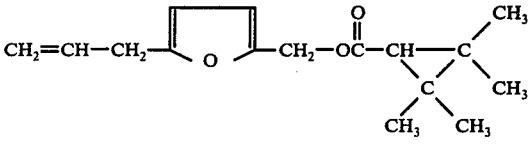 | >30 | 0 |
| Compound of "Farkaš et al; Chem. listy, 52 688-94 (1958)": | | |
| 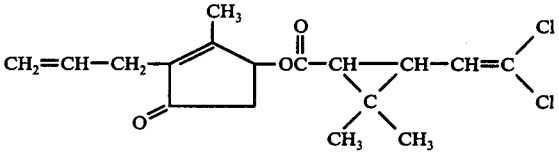 | >30 | 0 |
| Compound of German Offenlegungsschrift No. 2,326,077: | | |
| 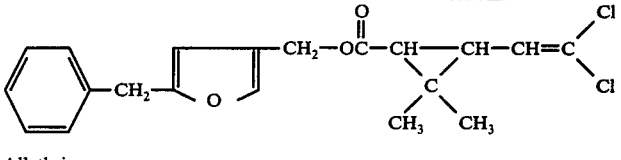 | >30 | 0 |
| Allethrin | >30 | 0 |

Test Example 3

20 Parts of each of the present compounds, compounds of U.S. Pat. No. 3,862,174, U.S. Pat. No. 3,795,696, U.S. Pat. No. 3,567,740, "Farkaš et al; Chem. listy, 52 688-94 (1958)", German Offenlegungsschrift No. 2,326,077, allethrin and meobal (3,4-dimethylphenyl-N-methylcarbamate), 20 parts of a surface active agent ("Sorpol SM-200", manufactured by Toho Kagaku Co., Ltd.) and 60 parts of xylene were mixed with stirring to make a 20% emulsion preparation.

About 20 rice seedlings, cultivated for 20 days after sowing in a flower pot of 8.5 cm in diameter, were sprayed in the ratio of 10 ml/pot with each of the emulsion which was obtained by diluting the above 20% emulsion preparation to 400 times with water. After air-drying, each pot was covered with a wire net cage, into which about 20 adults of smaller brown plant-hopper were released 1 day and 6 days after spraying, and the observation was made after 24 hours to obtain a mortality.

The results obtained are as shown in Table 4 below.

Table 4

| Test Compound | Mortality (%) | |
|---|---|---|
| | After 1 day | After 6 days |
| The present compound 31 | 100 | 75.8 |
| The present compound 32 | 100 | 100 |
| The present compound 36 | 100 | 65.3 |
| The present compound 39 | 100 | 85.0 |
| The present compound 40 | 100 | 66.7 |
| The present compound 48 | 100 | 55.0 |

Table 4-continued

| Test Compound | Mortality (%) After 1 day | After 6 days |
|---|---|---|
| The present compound 53 | 100 | 60.0 |
| The present compound 55 | 100 | 60.0 |
| The present compound 59 | 100 | 100 |
| The present compound 60 | 100 | 50.0 |
| The present compound 62 | 100 | 100 |
| The present compound 63 | 100 | 53.3 |
| The present compound 131 | 100 | 100 |
| The present compound 132 | 100 | 95.0 |
| The present compound 152 | 100 | 73.3 |
| The present compound 158 | 100 | 50.0 |

Compounds of U.S. Pat. No. 3,862,174:

[structure] — 95.0, 10.0

[structure] — 100, 35.0

[structure] — 100, 15.0

[structure] — 100, 5.0

Compounds of U.S. Pat. No. 3,795,696:

[structure] — 100, 35.0

Compounds of U.S. Pat. No. 3,567,740:

[structure] — 100, 29.7

[structure] — 100, 20.0

Compound of "Farkaš et al; Chem. listy, 52 688-94 (1958)":

[structure] — 95.0, 5.0

Table 4-continued

| Test Compound | Mortality (%) After 1 day | After 6 days |
|---|---|---|
| Compound of German Offenlegungsschrift No. 2,326,077: | 100 | 45.0 |
| Allethrin | 90.0 | 0.0 |
| Meobal | 100 | 40.0 |

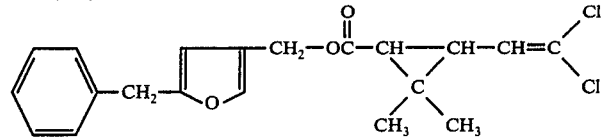

In preparing the insecticidal compositions of the present invention, the present compounds may be formulated into oil sprays, emulsifiable concentrates, dusts, aerosols, wettable powders, granules, mosquito coils and other heating or non-heating fumigants according to the procedures thoroughly known to those skilled in the art, using diluting adjuvants for general insecticides like in the case of the conventional pyrethroides. Alternatively, they may be formulated into death-inducing power or solid preparations incorporated with baits or other substances attractive for injurious insects.

Further, the present compounds can display more excellent insecticidal activities when used in combination of 2 or more, and can be enhanced in insecticidal effect when used in admixture with such synergists for pyrethroides as α-[2-(2-butoxyethoxy)-ethoxy]-4,5-methylenedioxy-2-propyltoluene (hereinafter referred to as "Piperonyl butoxide"), 1,2-methylenedioxy-4-[2-(octylsulfinyl)propyl]benzene (hereinafter referred to as "Sulfoxide"), 4-(3,4-methylenedioxyphenyl)-5-methyl-1,3-dioxane (hereinafter referred to as "Sufroxane"), N-(2-ethylhexyl)-bicyclo[2,2,1]hepta-5-ene-2,3-dicarboximide (hereinafter referred to as "MGK-264"), octachlorodipropyl ether (hereinafter referred to as "S-421") and isobornyl thiocyanoacetate (hereinafter referred to as "Thanite"), or with other known synergists effective for allethrin and pyrethrin.

When phenol derivatives such as BHT, bis-phenol derivatives, or arylamines such as phenyl-α-naphthylamine, phenyl-β-naphthylamine and phenetidineacetone condensates are added in suitable amounts as stabilizers, it is possible to obtain insecticidal compositions which have been more stabilized in effectiveness.

Furthermore, the present compounds may be used in admixture with other physiologically active materials, e.g. pyrethrin (pyrethrum extract), other known cylopropanecarboxylic acid ester type insecticides such as allethrin, N-(chrysanthemoxymethyl)-3,4,5,6-tetrahydrophthalimide (hereinafter referred to as "Tetramethrin"), 5-benzyl-3-furylmethyl chrysanthemate (hereinafter referred to as "Resmethrin"), 5-benzyl-3-furylmethyl chrysanthemate and geometrical or optical isomers thereof, organo-chlorine type insecticides such as DDT, BHC and methoxychlor, organo-phosphorus type insecticides such as O,O-dimethyl-O-(3-methyl-4-nitro-phenyl)-phosphorothioate (hereinafter referred to as "fenitrothion"), O,O-dimethyl-O-(2,2-dichlorovinyl)-phosphate (hereinafter referred to as DDVP), O,O-dimethyl-O3-methyl-4-methylmercaptophenyl phosphorothioate (trademark: Baycid), O,O-diethyl-O-1-(2',4'-dichlorophenyl)-2-chloro-vinyl phosphate (trademark: Vinyphate), dimethyldicarbethoxyethyl dithiophosphate (trademark: Malathion), 2-methoxy-4H-1,3,2-benzodioxaphosphorin-2-sulfide (trademark: Salithion), ethyldimethyldithiophosphorylphenyl acetate (trademark: Papthion), dimethyl-p-cyanophenyl thiophosphate (trademark: Cyanox), O,O-dimethyl-1-hydroxy-2,2,2-trichloroethyl phosphonate (trademark: Dipterex), and 2-isopropyl-4-methylpyrimidyl-6-diethylthiophosphate (trademark: Diazinon), carbamate type insecticides such as 1-naphthyl-N-methylcarbamate, 3,4-dimethylphenyl-N-methylcarbamate, 3,5-dimethylphenyl-N-methylcarbamate, 2-isopropoxyphenyl-N-methylcarbamate (trademark: Suncide), and S-methyl-N-[(methylcarbamoyl)oxy]thioacetimidate (trademark: Lannate), such insecticides as N'-(2-methyl-4-chlorophenyl)-N,N-dimethyl formamidine (trademark Galecron) and 1,3-bis(carbamoylthio)-2-(N,N-dimethylamino)propane hydrochloride (trademark: Cartap) or with other agricultural chemicals such as fungicides, nematocides, acaricides, herbicides, fertilizers, etc., whereby multi-purpose compositions excellent in effectiveness can be prepared, and synergistic effects due to blending therewith may be expected.

The present invention will be explained in more detail with reference to the following examples which are only illustrative, and not limitative.

Preparation of the insecticidal composition containing a cyclopropanecarboxylate [I]:

Example A

The cyclopropanecarboxylate [I] (Compound No. 2, 4, 5, 14, 16, 20, 21, 24, 28, 71, 72, 90, 91, 92, 93, 94, 102, 103, 106, 110, 114, 121, 126 130, 131 - 139, 142 - 144, 153 - 156, 158 - 160) 0.2 part by weight) was dissolved in kerosene (99.8 parts by weight) to make an oil preparation.

Example B

The cyclopropanecarboxylate [I] (Compound No. 31 - 63, 157) (1 part by weight) was dissolved in kerosene (99 parts by weight) to make an oil preparation.

Example C

The cyclopropanecarboxylate [I] (Compound No. 10, 11, 13, 15, 19, 22, 23, 25, 102 - 125) (0.5 part by weight) was dissolved in kerosene (99.5 parts by weight) to make an oil spray.

Example D

The cyclopropanecarboxylate [I] (Compound No. 1 - 5, 7, 9, 10 - 12, 14, 16 - 18, 20 - 26, 28, 71, 72, 86, 89, 94, 95, 102 - 106, 110 - 112, 121, 122) (0.1 part by weight) and piperonyl butoxide (0.5 part by weight) were dissolved in kerosene (99.4 parts by weight) to make an oil preparation.

Example E

The cyclopropanecarboxylate [I] (Compound No. 31 - 37, 39, 40 - 42, 44 - 48, 50 - 52, 54, 62) (0.3 part by weight) and piperonyl butoxide (1.5 parts by weight)

were dissolved in kerosene (98.2 parts by weight) to make an oil preparation.

Example F

The cyclopropanecarboxylate [I] (Compound No. 1 – 5, 8, 16, 27, 31 – 33, 36, 37, 102 – 106, 109, 116, 117, 126 – 130, 153, 157) (0.1 part by weight) and DDVP (0.2 part by weight) were dissolved in kerosene (99.7 parts by weight) to make an oil preparation.

Example G

The cyclopropanecarboxylate [I] (Compound No. 67 – 70, 76 – 83, 98 – 101, 156, 159) (0.2 part by weight) and DDVP (0.2 part by weight) were dissolved in kerosene (99.6 parts by weight) to make an oil preparation.

Example H

The cyclopropanecarboxylate [I] (Compound No. 1 – 4, 16, 20, 28, 71, 72, 90, 91, 92, 94, 95, 102 – 125, 126 – 130, 142 – 144, 154, 157) (10 parts by weight), S-421 (20 parts by weight), a surface active agent ("Sporpol SM-200", manufactured by Toho Kagaku Co., Ltd.) (15 parts by weight) and xylene (55 parts by weight) were mixed together to make an emulsion preparation.

Example I

The cyclopropanecarboxylate [I] (Compound No. 31 – 33, 46, 50, 53, 131, 132, 135 – 140, 155) (5 parts by weight), Sufroxan (15 parts by weight), a surface active agent ("Sorpol SM-200", manufactured by Toho Kagaku Co., Ltd.) (10 parts by weight) and xylene (70 parts by weight) were mixed together to make an emulsion preparation.

Example J

To the cyclopropanecarboxylate [I] (Compound No. 2, 31, 71, 102, 109, 120, 153) (0.4 part by weight), Chryson (trademark of Sumitomo Chemical Company, Limited) (0.2 part by weight) was added. The resultant mixture was admixed with xylene (7 parts by weight) and deodorized kerosene (7.4 parts by weight) and charged into an aerosol vessel. The vessel was provided with a valve means, and an atomizer (liquefied petroleum gas) (85 parts by weight) was charged into the vessel through the said valve means to make an aerosol preparation.

Example K

The cyclopropanecarboxylate [I] (Compound No. 4, 39, d-trans-chrysanthemic acid ester of 71, 111, 126 – 130, 154) (0.4 part by weight), piperonyl butoxide (2.0 parts by weight), xylene (6.2 parts by weight) and deodorized kerosene (7.0 parts by weight) were mixed together and charged into an aerosol vessel as in Example J to make an aerosol preparation.

EXAMPLE L

The cyclopropanecarboxylate [I] (Compound No. 21, 40, 94, 104, 122, 131, 132, 135 – 140) (0.3 part by weight), Chrysron (0.1 part by weight), Thanite (2.0 parts by weight), xylene (6 parts by weight) and deodorized kerosene (6.6 parts by weight) were mixed together and charged into an aerosol vessel as in Example J to make an aerosol preparation.

Example M

The cyclopropanecarboxylate [I] (Compound No. 94, 109, d-trans-chrysanthemic acid ester of 2, 32) (0.2 part by weight), tetramethrin (0.2 part by weight), piperonyl butoxide (2 parts by weight), xylene (6 parts by weight) and deodorized kerosene (6.6 parts by weight were mixed together and charged into an aerosol vessel as in Example J to make an aerosol preparation.

Example N

The cyclopropanecarboxylate [I] (Compound No. 11, 46, 92, 110, 121, 153) (0.4 part by weight), Fenitrothion (0.5 part by weight), xylene (7 parts by weight) and deodorized kerosene (7.1 parts by weight) were mixed together and charged into an aerosol vessel as in Example J to make an aerosol preparation.

Example O

The cyclopropanecarboxylate [I] (Compound No. 111, d-trans-chrysanthemic acid ester of 4, 71, d-cis-chrysanthemic acid ester of 31, 38, 46, 153 (0.4 part by weight), piperonyl butoxide (2 parts by weight), deodorized kerosene (11.6 parts by weight) and an emulsifier ("Atmos 300"; manufactured by Atlas Chemical Co., Ltd.) (1 part by weight) were mixed together, and water (50 parts by weight) was added thereto. The resulting emulsion was charged with a 3 : 1 mixture of deodorized butane and deodorized propane (35 parts by weight) into an aerosol vessel to make a water-base aerosol preparation.

Example P

The cyclopropanecarboxylate [I] (Compound No. each d-cis form of (1, 2, 4, 5, 11 – 13, 20 – 24, 71, 72), 102, 103, 105, 106, 112 – 114, 116, 117, 123, 154, 157) (0.5 g) was dissolved in methanol (20 ml), and the resultant solution was admixed uniformly with a carrier for mosquito coil consisting of Pyrethrum marc., Tabu powder and wood powder in a weight ratio of 5 : 3 : 1 (99.5 g). After evaporation of methanol, the residue was kneaded well with water (150 ml), shaped and dried to make a mosquito coil.

Example Q

The cyclopropanecarboxylate [I] (Compound No. d-cis form of 31, 37, 46) (0.8 g) was dissolved in methanol (20 ml), and the resultant solution was admixed uniformly with a carrier for mosquito coil consisting of Pyrethrum marc., Tabu powder and wood powder in a weight ratio of 5 : 3 : 1 ( 99.2 g). After evaporation of methanol, the residue was kneaded well with water (150 ml), shaped and dried to make a mosquito coil.

Example R

The cyclopropanecarboxylate [I] (Compound No. 1, 2, 4, 11, 12, 21, 27, 31, 64, 65, 71 – 75, 86, 90, 102, 103, 105, 111, 112, 116, 122) (0.3 g) and allethrin (0.3 g) were dissolved in methanol (20 ml), and the resulting solution was treated in Example P to make a mosquito coil.

Example S

A sheet of asbestos of 2.5 cm in length, 1.5 cm in width and 0.3 mm in thickness was dipped in a solution of the cyclopropanecarboxylate [I] (Compound No. 102, 109, d-trans form of 4) (0.05 g) in chloroform to make an insecticidal fumigant preparation which was used by heating on a hot plate.

As a fibrous carrier, a pulp plate with the same effects as asbestos may be used.

Example T

A sheet of asbestos of 3.5 cm in length, 1.5 cm in width and 0.3 mm in thickness was dipped in a solution of the cyclopropanecarboxylate [I] (Compound No. 2, 4, 5, 11, 12, 21, 65, 71, 72, 86, 89 – 91, 102, 105, 109, 111, 116, 153) (0.1 g), d-transallethrin (0.02 g), BHT (0.05 g) and piperonyl butoxide (0.1 g) in chloroform to make an insecticidal fumigant preparation which was used by heating on a hot plate. As a fibrous carrier, a pulp plate with the same effects as asbestos may be used.

Example U

The cyclopropanecarboxylate [I] (Compound No. 24, 28, 94, 95, 102, 109, 111, d-trans form of 2, 4, 71, 72, 155, 158) (1 part by weight), Safroxane (3 parts by weight), acetone (20 parts by weight) and 300 mesh diatomaceous earth (96 parts by weight) were mixed well and the acetone was evaporated therefrom to make a dust preparation.

Example V

The cyclopropanecarboxylate [I] (Compound No. 16, 31, 71, 103, 106, 116, 122, 156, 160) (20 parts by weight), 1-naphthyl-N-methylcarbamate (5 parts by weight), an emulsifier ("Sorpol SM-200") (5 parts by weight) and 300 mesh talc (70 parts by weight) were mixed well to make a wettable powder preparation.

Example W

The cyclopropanecarboxylate [I] (Compound No. 4, 31, 32, 96, 102, 111, 114, 122, 157) (3 parts by weight), 5-propargylfurfuryl chrysanthemate (2 parts by weight), sodium ligninsulfonate ("Toyolignin CT"; manufactured by Toyo Boseki Kabushiki Kaisha) (5 parts by weight) and clay ("GSM clay"; manufactured by Zieklite Kogyo Co., Ltd.) (90 parts by weight) were mixed well.

The resulting mixture was admixed with 10% by weight of water, granulated and dried to give a granule preparation.

Example X

The cyclopropanecarboxylate [I] (Compound No. 1 – 28, 31 – 35, 39 – 43, 45 – 48, 50, 53 – 63, 64 – 98, 131 – 141, 102 – 125, 142 – 144, 158) (20 parts by weight), an emulsifier ("Sorpol SM-200") (20 parts by weight) and xylene (60 parts by weight) were mixed well to make an emulsion preparation.

Example Y

The cyclopropanecarboxylate [I] (Compound No. 2, 4, 12, 21, 64, 65, 67, 71 – 75, 86, 89, 93, 101, 110, 120) (0.05 g), 5-propargyl-2-methyl-3-furylmethyl chrysanthemate (0.02 g), BHT (0.2 g), piperonyl butoxide (0.05 g) were mixed to make an insecticidal fumigant preparation according to Example S which was used by heating on a hot plate.

Insecticidal effect of the insecticidal composition containing the cyclopropanecarboxylate [I] is as follows:

Example I

The oil preparation (5 ml) obtained as in Example, A, C, D, F or G was sprayed by the use of a Campbell's turn table [Soap & Sanitary Chemicals, Vol. 14, No. 6, 119 (1938)] on 100 adults of housefly, and the houseflies were exposed under the spray for 10 minutes. The houseflies were then allowed to stand with feeding. On the next day, the death of more than 80% was confirmed.

Example II

In a glass chamber of 70 cm cube, 50 adults of mosquito were released. 0.7 Milliliters of the oil preparation obtained as in Example F was sprayed with the glass atomizer at a pressure of 20 pounds and within 10 minutes thereafter more than 80% of the mosquitos were knocked down. On the next day, the death of more than 80% was confirmed for each oil preparation.

Example III

The emulsion preparation obtained as in Example H was diluted with water to make a 10,000 fold dilution. The dilution (2 liters) was charged in a case of 23 cm in length, 30 cm in width and 6 cm in depth, and 100 larvae of mosquito were release therein. On the next day, the death of more than 90% was confirmed.

Example IV

In a glass chamber of 70 cm cube, 50 adults of mosquito were released. A small electric fan of 13 cm in diameter equipped in the chamber was driven, and the mosquito coil (0.1 g) obtained as in Example P or R was ignited at both ends and placed therein. More than 80% of the mosquitos was knocked down within 20 minutes. On the next day, the death of more than 80% was confirmed.

Example V

In a glass chamber of 70 cm cube, 50 adults of housefly were released. A small electric fan of 13 cm in diameter equipped in the chamber was driven, and the fumigant preparation obtained as in Example S, T or Y was placed on a hot plate therein. More than 80% of the mosquitos was knocked down within 20 minutes.

EXAMPLE VI

The insecticidal potency of the aerosol preparation obtained as in Example J, K, L, M, N or O against adults of housefly was tested according to the aerosol test method using Peet Grady chamber (6 feet)$^3$ as described in Soap & Chemical Specialities Bluebook (1965). More than 80% of houseflies were knocked down within 15 minutes after spraying. On the next day, the death of more than 70% was confirmed.

EXAMPLE VII

The dust preparation obtained as in Example U was uniformly dispersed on a Petri dish of 14 cm in diameter to make a layer in the rate of 2 g/m$^2$ on the bottom. On the wall of the Petri dish, butter was applied remaining about 1 cm from the bottom. The adults of cockroach were released therein and contacted with the Petri dish for 30 minutes. Three days after the contact, more than 70% of the cockroaches were dead.

EXAMPLE VIII

The emulsion preparation obtained as in Example X was diluted with water to make a 100 fold dilution. The dilution (10 ml) was sprayed on rice plants cultivated for 45 days after seeding in a 1/50,000 Wagner pot. Then, the pot was covered with a net, and 30 adults of green rice leafhopper were released therein. After one day, more than 70% of the green rice leafhoppers were killed.

Table 6

| Test compound | Mortality (%) |
|---|---|
| 31 | 92 |
| 32 | 96 |
| 62 | 93 |
| 63 | 95 |
| 136 | 90 |
| 137 | 100 |
| 138 | 100 |
| 139 | 95 |
| 158 | 87 |

EXAMPLE XX

An emulsion prepared by diluting with water the present compounds 31, 32, 33, 34, 35, 46, 63, in the form of an emulsifiable concentrate was orally administered to male mice of about 20 g in body weight. From the alive and dead of the mice during 48 hours, $LD_{50}$ value was calculated. The results obtained are shown in the following Table.

Table 7

| Test compound | $LD_{50}$ (mg/kg) |
|---|---|
| 31 | > 500 |
| 32 | > 500 |
| 33 | > 600 |
| 34 | > 600 |
| 35 | > 600 |
| 46 | > 600 |
| 63 | > 600 |

EXAMPLE XXI

The oil preparation of the present compounds 31, 62, 131, 132, 133, 134, 135, 139, obtained as in Example A having different concentrations were sprayed by the use of a Campbell's turn table [Soap & Sanitary Chemicals, Vol. 14, No. 6, 119 (1938)] on 100 adults of houseflies were exposed to the spray for 10 minutes. The houseflies were then allowed to stand with feeding. On the next day, dead and alive were counted to calculate $LD_{50}$.

The results obtained are as shown in the following table.

Table 8

| Test compound | $LD_{50}$ (mg/100 ml) |
|---|---|
| 31 | 250 |
| 62 | 210 |
| 131 | 52 |
| 132 | 32 |
| 133 | 50 |
| 134 | 100 |
| 135 | 98 |
| 139 | 86 |
| Allethrin | 350 |

What is claimed is:

1. Alkynyl esters of cyclopropanecarboxylic acid represented by the formula (I),

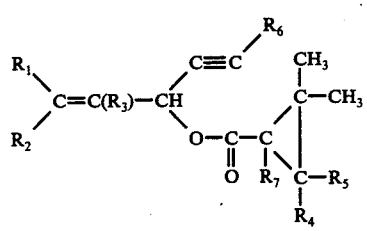

wherein $R_1$ represents hydrogen, lower alkyl having 1 - 4 carbon atoms, lower alkenyl having 2 - 4 carbon atoms, lower alkynyl having 2 - 4 carbon atoms, $C_1$-$C_2$ alkoxy-$C_1$-$C_4$ alkyl, $C_1$-$C_2$ alkylthio-$C_1$-$C_4$ alkyl, furyl, thienyl, furfuryl, thenyl, cyclo-$C_3$-$C_6$-alkyl, cyclo-$C_5$ alkyl containing an oxygen atom in the ring, cyclo-$C_5$-$C_6$ alkenyl, cyclo-$C_4$-$C_5$ alkenyl containing an oxygen atom in the ring or

in which X is halogen, nitro, cyano, methylenedioxy, $C_1$-$C_3$ alkyl, $C_1$-$C_2$ alkoxy, dimethylamino, n is 0, 1 or 2 and each X may be different when n is 2; $R_2$ and $R_3$ individually represent hydrogen, halogen (except $R_2$), phenyl, benzyl, lower alkyl having 1 - 3 carbon atoms, lower alkenyl having 1 - 3 carbon atoms, lower alkenyl having 2 - 3 carbon atoms or may form a carbon-carbon bond or are bonded to each other at the ends to form $C_3$-$C_4$ polymethylene chain or $R_1$ and $R_2$ are bonded to each other at the ends to form $C_5$ polymethylene chain; $R_4$ represents hydrogen or methyl; $R_5$ represents hydrogen, methyl, vinyl, 1-propenyl, 2-methyl-1-propenyl, 2-methoxymethyl-1-propenyl, 2-methoxycarbonyl-1-propenyl, or cyclopentylidenemethyl when $R_4$ is hydrogen, and $R_5$ represents methyl when $R_4$ is methyl; and $R_6$ and $R_7$ represent hydrogen or methyl.

2. A compound of the formula,

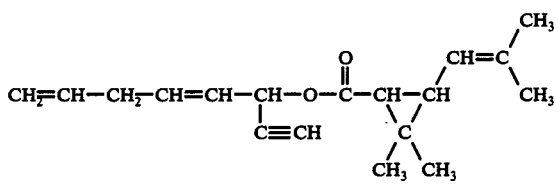

3. A compound of the formula,

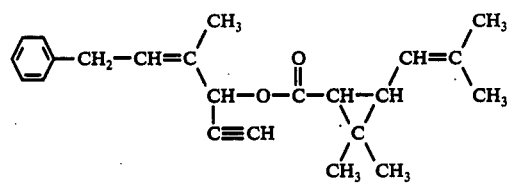

4. A compound of the formula,

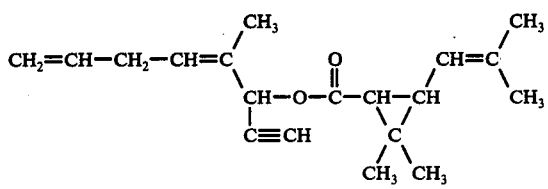

5. A compound of the formula,

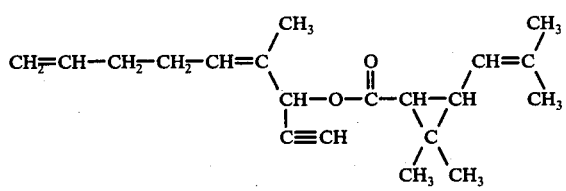

6. A compound of the formula,

EXAMPLE IX

About 20 rice seedlings, cultivated for 20 days after sowing in a flower pot of 8.5 cm in diameter, were sprayed with each of the emulsifiable concentrates and wettable powder obtained in Examples H, V or X which were diluted to 200 times with water. After air-drying, each pot was covered with a wire cage, and 30 adults of planthoppers were released therein. The observation was made after 24 hrs. As a result, more than 80% of planthoppers were dead in each case.

EXAMPLE X

Ten of the 3rd or 4th instar larvae of tobacco cut worm were put into a Petri dish of 17 cm in diameter.

One ml of the present compound (4, 11, 28, 92, 94, 95, 109, 111) in the form of an emulsion obtained in Example X, which were diluted to 50 times with water, were sprayed by means of a settling tower. The said larvae were removed into another Petri dish with the leaves of the chinese cabbage leaves. Observation was made after 48 hrs. As a result, more than 90% of the larvae were dead in each case.

EXAMPLE XI

One gram of the granular composition obtained as in Example W was put into 10l of water in a 14l pail made of polyethylene. After one day, about 100 full-grown larvae of Northern house mosquito were released into the said water. In 24 hrs., more than 90% of the mosquito larvae were dead.

EXAMPLE XII

Mottled kidney bean plants at 2 leaves-stage, which had elapsed 9 days after sowing, were parasitized with 10 to 15 carbmine mites per leaf, and left in a room at 27° C for a week.

Then each of the emulsifiable concentrate obtained as in Example X were diluted to 500 times with water and the dilutions were sprayed with 10 ml per pot on the turn table.

The observation was made after 10 days. As a result, the increased damage of the said plant was not found in each case.

EXAMPLE XIII

Rice plants at the tillering stage were grown in Wagner pots, and the depth of water was kept at 5 cm.

The present compound (4) obtained in Example W was put into the Wagner pot with 10 kg/10 ares, and the said pot was covered with a wire cage into which 20 adult leafhoppers were released.

As a result, more than 90% of leafhoppers were dead after 24 hrs.

EXAMPLE XIV

In the vinyl house, the Chinese cabbages were cultivated and the leaves were parasitized with the larvae of tobacco cut worm, diamondback moth and common cabbage worms.

The vinyl house (its height was 2 m) was divided into compartments of 30 m² in area and 10 grams of the present compound (1 or 4) in the form of 40% wettable powder was put into the plate heated by fire.

As a result, the increasing of the damage was not found in each case.

EXAMPLE XV

About 20 rice seedlings, cultivated for 20 days after sowing in a flower pot of 8.5 cm in diameter were sprayed with each of the present compounds (31, 32, 35, 39, 40, 42, 45, 48, 55, 59, 60, 63, 131 – 134, 139) in the form of an emulsion which were diluted to 50 times. Each pot as put into the beaker and covered with gauze, into which leafhoppers of resistant and susceptible strains, respectively, were released in each beaker. And the number of knocked down insects after 1 hour and the mortality after 24 hours were counted. As a result, the knock down per-centage was more than 50% and the mortality was more than 80% in each case.

EXAMPLE XVI

Each of the emulsifiable concentrates obtained in Example X was diluted to 100 times their volume with water.

The resulting solution was sprayed to potted Chinese cabbages at their 5 – 6 leaf stage in a proportion of 10 ml per pot.

After air-drying, 4th instar larvae of diamondback moths were parasitized on the leaves. After 24 hours, more than 80% of the larvae were dead in each case.

EXAMPLE XVII

Each 5% dust of the present compounds 31, 32, 62, 63 was spread in a ratio of 3 kg/10 ares on the Chinese cabbages of 40 days after sowing in the field. And about 9,000 eggs of tobacco cut worm were put on the leaves of the Chinese cabbages per 10 ares every 5 days for a month.

As a result, the damage of the Chinese cabbages by tobacco cut worms was not found in the field of the Chinese cabbages for 2 months.

EXAMPLE XVIII

30 Full grown larvae of the Northern house mosquito were released into the beaker with 200 ml of dilution of each emulsifiable concentrates which obtained in Example X.

After 24 hours, the death and alive were observed to culculate $LC_{50}$.

The results obtained are as shown in the following Table 5.

Table 5

| Test compound | Value of $LC_{50}$ (ppm) |
|---|---|
| 31 | 0.12 |
| 32 | 0.069 |
| 33 | 0.34 |
| 34 | 0.14 |
| 62 | 0.034 |
| 63 | 0.14 |

EXAMPLE XIX

The oil preparation (5 ml) obtained as in Example B was sprayed by the use of a Campbell's turn table [Soap & Sanitary Chemicals, Vol. 14, No. 6, 119 (1938)] on 100 adults of houseflies were exposed to the spray for 10 minutes. The houseflies were then allowed to stand with feeding. On the next day, dead and alive were observed.

The results obtained are as shown in the following Table.

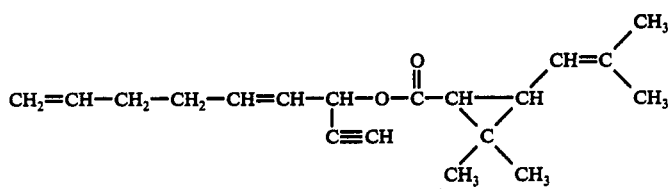

7. A compound of the formula,

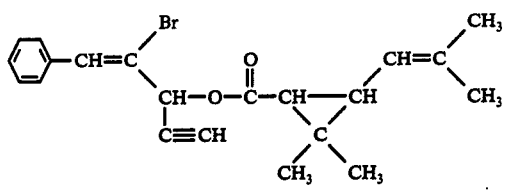

8. A compound of the formula,

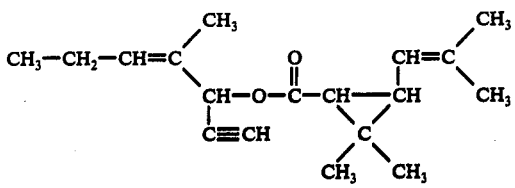

9. A compound of the formula,

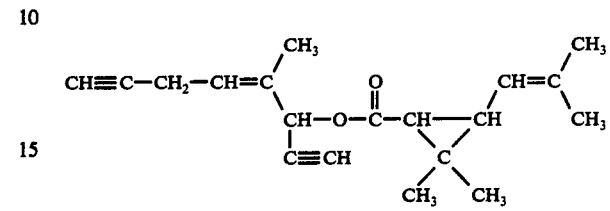

10. A compound of the formula,

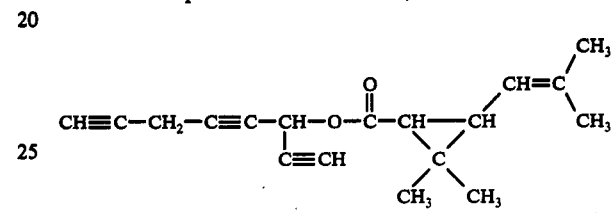

11. A compound of the formula,

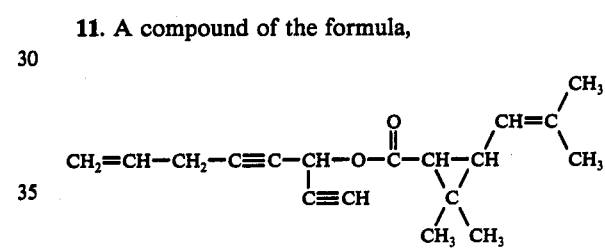

12. An insecticidal composition which comprises as an active ingredient an effective amount of at least one cyclopropanecarboxylate as claimed in claim 1, and an inert carrier.

13. A method for controlling harmful insects which comprises applying the cyclopropanecarboxylate as claimed in claim 1 to the insects.

* * * * *